United States Patent [19]

Cockerill, III et al.

[11] Patent Number: 5,658,733
[45] Date of Patent: *Aug. 19, 1997

[54] DETECTION OF ISONIAZID RESISTANT STRAINS OF M. TUBERCULOSIS

[75] Inventors: Franklin R. Cockerill, III; Bruce C. Kline; James R. Uhl, all of Rochester, Minn.

[73] Assignee: Mayo Foundation For Medical Education And Research, Rochester, Minn.

[*] Notice: The portion of the term of this patent subsequent to Apr. 18, 2014, has been disclaimed.

[21] Appl. No.: 418,782

[22] Filed: Apr. 7, 1995

Related U.S. Application Data

[63] Continuation-in-part of Ser. No. 228,662, Apr. 18, 1994.
[51] Int. Cl.$^6$ ............................. C12Q 1/68; C12P 19/34; C07H 21/04; C12N 15/00
[52] U.S. Cl. ...................... 435/6; 435/91.1; 435/91.2; 435/863; 536/23.7; 536/24.32; 536/24.33; 935/8; 935/76; 935/77; 935/78
[58] Field of Search ........................ 435/6, 91.1, 91.2, 435/172.1, 270, 863, 183; 536/23.7, 24.32, 24.33; 935/8, 76, 77, 78; 356/344

[56] References Cited

FOREIGN PATENT DOCUMENTS

88/03957  6/1988  WIPO ............................ C12Q 1/68
WO93/22454  11/1993  WIPO .

OTHER PUBLICATIONS

Sigma Molecular Biology Catalog, p. 54. 1989.
Ying Zhang et al., "The catalase–peroxide gene and isoniazid resistance of Mycobacterium tuberculosis," Nature, vol. 358, pp. 591–593. Aug. 13, 1992.
R.E. Chaisson et al., "Tuberculosis in Patients with the Acquired Immunodeficiency Syndrome," Am. Res. Resp. Dis., 136, 570–574 (1987).
F.R. Cockerill, III, et al., "Rapid Identification of a Point Mutation of the Myobacterium tuberculosis Catalase–Peroxidase (katG) Gene Associated with Isoniazid Resistance", Journal of Infectious Diseases, 171, 240–245 (Jan. 1995).
S.W. Dooley et al., "Multidrug–resistant Tuberculosis," Ann. Int. Med., 117, 257 (Aug. 1, 1992).
K. D. Eisenach et al., "Polymerase Chain Reaction Amplification of a Repetitive DNA Sequence Specific for Mycobacterium tuberculosis", J. Infect. Dis., 161, No. 4, 997 (Apr. 1990).

M. A. Fischl et al., "An Outbreak of Tuberculosis Caused by Multiple–Drug–resistant Tubercle Bacilli among Patients with HIV Infection," Ann. Int. Med., 117, 177 (Aug. 1, 1992).
B. Heym et al., "Missense mutations in the catalase–peroxidase gene, katG, are associated with isoniazid resistance in Mycobacterium tuberculosis", Molecular Biology, 15, 235–245 (1995).
B. Heym et al., "Characterization of the KatG Gene Encoding a Catalase–Peroxidase Required for the Isoniazid Susceptibility of Mycobacterium tuberculosis" J. Bacteriol., 175, No. 13, 4255 (Jul. 1993).
G. Middlebrook, "Isoniazid–Resistance and Catalase Activity of Tubercle Bacilli," Am. Rev. Tuberc., 69, 471 (1954).
N. Miller et al., "Evaluation of the Gen–Probe Amplified Mycobacterium tuberculosis Test (GPA–tb) and the Polymerase Chain Reaction (PCR) on Patients with Pulmonary Tuberculosis," Abstracts ASM, Abstract No. U–48, Atlanta, GA (1993) at p. 177.
M. L. Pearson et al., "Nosocomial Transmission of Multidrug–resistant Mycobacterium tuberculosis. A Risk to Patients and Health Care Workers," Ann. Int. Med., 117, 191 (Aug. 1, 1992).
D. Snider, "Research Towards Global Control and Prevention of Tuberculosis with an Emphasis on Vaccine Development," Rev. Inf. Dis., vol. II, S336–337 (Mar./Apr. 1989).
D.E. Snider, Jr., et al., "The New Tuberculosis," New Engl. J. Med., 326, No. 10, 703 (1992).
K. Takayama et al., "Isonicotinic Acid Hydrazide," Mechanism of Action of Antibacterial Agents, Ed. F. E. Hahn, Springer–Verlag (1979) at pp. 98–119.
J. Youatt, "A Review of the Action of Isoniazid," Am. Rev. Resp. Dis., 99, 729 (1969).
Ying Zhang et al., "The catalase–peroxide gene and isoniazid resistance of Mycobacterium tuberculosis," Nature, 358, 591 (Aug. 13, 1992).
Ying Zhang et al., "Transformation with KatG restores isoniazid–sensitivity in Mycobacterium tuberculosis isolates resistant to a range of drug concentrations," Molec. Microbiol., 8(3), 521 (1993).

Primary Examiner—Bradley L. Sisson
Attorney, Agent, or Firm—Schwegman, Lundberg, Woessner & Kluth, P.A.

[57] ABSTRACT

A method for determining the susceptibility of a strain of M. tuberculosis to isoniazid is provided comprising employing the techniques of restriction fragment length polymorphism analysis to determine whether or not the DNA of said strain has an MspI restriction site at the codon corresponding to codons 315 or 463 of an M. tuberculosis katG gene consensus sequence.

20 Claims, 15 Drawing Sheets

```
  61 AGGAATGcTGTGcCCGAGCAACACCCACCCATtACAGAaaccaccaCCGG 110
     ||||||||||||||||||||||||||||||||||||||||||||||||||
1970 AGGAATGCTGTGCCCGAGCAACACCCACCCATTACAGAAACCACCACCGG 2019

111 AGCCgCTAgCAACGgCTGTCCCGTCGTGGGTCATATGAAATACCCcgTCG 160
     ||||||||||||||||||||||||||||||||||||||||||||||||||
2020 AGCCGCTAGCAACGGCTGTCCCGTCGTGGGTCATATGAAATACCCCGTCG 2069

161 AGGGCGGcGGAAACCAGGACTGGTGgcCCAACCGgCTCAATCTGAAGGTA 210
     ||||||||||||||||||||||||||||||||||||||||||||||||||
2070 AGGGCGGCGGAAACCAGGACTGGTGGCCCAACCGGCTCAATCTGAAGGTA 2119

211 CTGCACCaAAACCCGgCCGTCGCTGAcCCGATGGGTGCGGCGTTCGACTA 260
     ||||||||||||||||||||||||||||||||||||||||||||||||||
2120 CTGCACCAAAACCCGGCCGTCGCTGACCCGATGGGTGCGGCGTTCGACTA 2169

261 TgCCgCGGAGGTCGCGACCATCGACGTTGACgCCCTGACGCGGGACATCG 310
     ||||||||||||||||||||    ||||||||||||||||||||||||||
2170 TGCCGCGGAGGTCGCGACCAGTCGACTTGACGCCCTGACGCGGGACATCG 2219

311 AGGAAGTGATGACCACCTCGCAgCCGTGgTGGCCCgcCGACTACGGCCAC 360
     ||||||||||||||||||||||||||||||||||||||||||||||||||
2220 AGGAAGTGATGACCACCTCGCAGCCGTGGTGGCCCGCCGACTACGGCCAC 2269

361 TACGGGCCGCTGTTTATCCGGATGGCGTGGCACGCTGCCGGCACCTACCG 410
     ||||||||||||||||||||||||||||||||||||||||||||||||||
2270 TACGGGCCGCTGTTTATCCGGATGGCGTGGCACGCTGCCGGCACCTACCG 2319

411 CATCCACGACGGCCGCGGCGGCGCCGGGGGCGGCATgCAGCgGTTCGCGC 460
     ||||||||||||||||||||||||||||||||||||||||||||||||||
2320 CATCCACGACGGCCGCGGCGGCGCCGGGGGCGGCATGCAGCGGTTCGCGC 2369

461 CGCTTAACAGCTGGCCCGACAACGCCAGCTTGGACAAGGCGCGCCGGcTG 510
     ||||||||||||||||||||||||||||||||||||||||||||||||||
2370 CGCTTAACAGCTGGCCCGACAACGCCAGCTTGGACAAGGCGCGCCGGCTG 2419

511 CTGTGGCCGGTCAAGAAGAAGTACGGCAAGAAGCTCTCATGGGCGGACCT 560
     ||||||||||||||||||||||||||||||||||||||||||||||||||
2420 CTGTGGCCGGTCAAGAAGAAGTACGGCAAGAAGCTCTCATGGGCGGACCT 2469

561 GATTGTTTTCgCCGgCAACTGC.GCGCT.GGAATCGATGGGCTTCAAGAC 608
     |||||||||||||||| || ||||| ||||||||||||||||||||||||
2470 GATTGTTTTCGCCGGCAACCGCTGCGCTCGGAATCGATGGGCTTCAAGAC 2519

609 GTTCGGGTTCGGCTTCGGCCGGGTCGACCAGTGGGAGCCCGATGAGGTCT 658
     ||||||||||||||||| | |||||||||||||||| |||||||||||||
2520 GTTCGGGTTCGGCTTCGG...GCGTCGACCAGTGGGAGACCGATGAGGTCT 2567

659 ATTGGGGCAAGGAAGCCACcTGgCTCGGCGATGAGCGTTACAGCGGTAAG 708
     ||||||||||||||||||||||||||||||||||| ||||||||| |||||
2568 ATTGGGGCAAGGAAGCCACCTGGCTCGGCGATGACGGTTACAGC.GTAAG 2616
```

FIG. 1A

```
 709 CGGGATCTGGAGAACCCgCTGgCCGCGGTGcAGATGGGGCTGATCTACGT  758
     |  ||||||||||||||||||||||||||||||||||||||||||||||||
2617 C..GATCTGGAGAACCCGCTGGCCGCGGTGCAGATGGGGCTGATCTACGT 2664

759 GaACCCGGAGGGGCCGAACGGCAACCCGGACCCCATGgCCGCGGCGGTCG  808
     ||||||||||| ||||||||||||||||||||||||| ||||||||||||
2665 GAACCCGGAGGCGCCGAACGGCAACCCGGACCCCATGGCCGCGGCGGTCG 2714

809 ACATTCGCGAGACGTTTCGGCGCATGGCCATGAaCGACGTCGAAACAgcG  858
     |||||||||||||||||||||||||||||||||| |||||||||||| ||
2715 ACATTCGCGAGACGTTTCGGCGCATGGCCATGAACGACGTCGAAACAGCG 2764

859 gcgCTGATCGTcGGCGGTCACACTTTCGGTAAGACCCATGGCgCCGGCCC  908
     |||||||||||| |||||||||||||||||||||||||||||| ||||||
2765 GCGCTGATCGTCGGCGGTCACACTTTCGGTAAGACCCATGGCGCCGGCCC 2814

909 GGcCGATCTGGTCGGCCCCGAACCCGAGGCTGCTCCGCTGGAGCAGATGG  958
     || |||||||||||||||||||||||||||||||||||||||||||||||
2815 GGCCGATCTGGTCGGCCCCGAACCCGAGGCTGCTCCGCTGGAGCAGATGG 2864

959 GCTTGGGCTGGAAGAGcTCGTATGgCACCGGAACCGGTAAGGACGCGATC 1008
     |||||||||||||||| ||||||| |||||||||||||||||||||||||
2865 GCTTGGGCTGGAAGAGCTCGTATGGCACCGGAACCGGTAAGGACGCGATC 2914

1009 ACCAgCGGCATCGAGGTCGTATGGACGAACACCCCGACGAAATGGGACAA 1058
     |||| |||||||||||||||||||||||||||||||||||||||||||||
2915 ACCAGCGGCATCGAGGTCGTATGGACGAACACCCCGACGAAATGGGACAA 2964

1059 CAGTTTCCTCGAGATCCTGTaCGGCTACGAGTGGGAGCTGACGAAGAGCC 1108
     ||||||||||||||||||||| ||||||||||||||||||||||||||||
2965 CAGTTTCCTCGAGATCCTGTACGGCTACGAGTGGGAGCTGACGAAGAGCC 3014

1109 CTGCTGGCGCTTGGCAATACACCGCCAAGGACGGCGCCGGTGCCGGCACC 1158
     ||||||||||||||||||||||||||||||||||||||||||||||||||
3015 CTGCTGGCGCTTGGCAATACACCGCCAAGGACGGCGCCGGTGCCGGCACC 3064

1159 ATCCCGGACCCGTTCGGcGGGCCAGGGCGCTCCCCGACGATGCTGGCCAC 1208
     ||||||||||||||||| ||||||||||||||||||||||||||||||||
3065 ATCCCGGACCCGTTCGGCGGGCCAGGGCGCTCCCCGACGATGCTGGCCAC 3114

1209 TGACCTCTCGCTGCGGGTGGATCCGATCTATGAGCGGATCACGCGTCGCT 1258
     ||||||||||||||||||||||||||||||||||||||||||||||||||
3115 TGACCTCTCGCTGCGGGTGGATCCGATCTATGAGCGGATCACGCGTCGCT 3164

1259 GGCTGGAACACCCCGAGGAATTGGCCGACGAGTTCGCCAAGGCCTGGTAC 1308
     ||||||||||||||||||||||||||||||||||   |||||||||||||
3165 GGCTGGAACACCCCGAGGAATTGGCCGACGAGTTCCGCAAGGCCTGGTAC 3214

1309 AAGCTGATCCACCGAGACATGGgTCCCGtTGcGAGATACCTTGGGcCGcT 1358
     |||||||||||||||||||||| ||||| || ||||||||||||| || |
3215 AAGCTGATCCACCGAGACATGGGTCCCGTTGCGAGATACCTTGGGCCGCT 3264
```

FIG. 1B

```
1359 GGTCCCCAAGcAGACCCTGcTGTGGcAGGATCCGGTCCCTGcGGTCAGCC 1408
     ||||||||||| ||||||||| |||||||||||||||||||| ||||||| |
3265 GGTCCCCAAGCAGACCCTGCTGTGGCAGGATCCGGTCCCTGCGGTCAG.C 3313

1409 ACGAcCTCGTCGGcGAAGcCGAGATTGCCAGCCTTAAGAGCCAGATCCgG 1458
     |||| |||||||| ||||  ||||||||||||||||||||||||||||||
3314 ACGACCTCGTCGGCGAAGC..AGATTGCCAGCCTTAAGAGCCAGATCCGG 3361

1459 GCATCGGGATTGACTGTCTCACAGCTAGTTTCGACCGCATGGGCGGCGGC 1508
     ||||||||||||||||||||||||||||||||||||||||||||||||||
3362 GCATCGGGATTGACTGTCTCACAGCTAGTTTCGACCGCATGGGCGGCGGC 3411

1509 GTCGTCGTTCCGTGGTAGCGACAAgCGCGGcGGCGCCAACGGTGGTCGCA 1558
     |||||||||||||||||||||||| |||||| ||||||||||||||||||
3412 GTCGTCGTTCCGTGGTAGCGACAAGCGCGGCGGCGCCAACGGTGGTCGCA 3461

1559 TCCgCCTGCAGCCACAAGTCGGGtGGGAGGTCAACGACCCCGACGGGGAT 1608
     ||| |||||||||||||||||||  |||||||||||||||||||  ||||
3462 TCCGCCTGCAGCCACAAGTCGGGTGGGAGGTCAACGACCCCGAC...GGAT 3509

1609 CTGCGCAAGGTCATTCGCACCCTGGAAGAGATCCAGGAGTCATTCAACTC 1658
     ||||||||||||||||||||||| ||||||||||||||||||||||
3510 CTGCGCAAGGTCATTCGCACCCT.GAAGAGATCCAGGAGTCATTCA.... 3554

1659 CGCGGCgCCGGGGAACATCAAAGTGTCCTTCGCCGACCTCGTCGTGCTCG 1708
     | ||||| |||||||||||||||||||||||||||||||||||||||||
3555 CTCGGCGC..GGGAACATCAAAGTGTCCTTCGCCGACCTCGTCGTGCTCG 3602

1709 GTGGCTGTGcCgCCATAGAGAAAGCAgCAAAGGCGGCTGGCCACAACATC 1758
     |||||||||| | |||||||||||||| ||||||||||||||||||||||
3603 GTGGCTGTGCGCCACTAGAGAAAGCAGCAAAGGCGGCTGGCCACAACATC 3652

1759 ACGGTgCCCTTCACCCCGGGCCGcACGGATGCgTCGCAGGAACAAACCGA 1808
     ||||| |||||||||||||||||| |||||| ||||||||||||||||||
3653 ACGGTGCCCTTCACCCCGGGCCCGCACGATGCGTCGCAGGAACAAACCGA 3702

1809 CGTGGAATCCTTTGCCGTGCTGGAGcCCAAGGCAGATGGCTTCCGAAACT 1858
     |||||||||||||||||||||||||| |||||||||||||||||||||||
3703 CGTGGAATCCTTTGCCGTGCTGGAGCCCAAGGCAGATGGCTTCCGAAACT 3752

1859 ACCTCGGAAAGGGCAACCCGTTGCCGGCCGAGTACAT.gCTgcTCGACAA 1907
     ||||||||||||| |||| |||||||||||||||||| || |||||||||
3753 ACCTCGGAAAGGGCAA..CCGTTGCCGGCCGAGTACATCGCTGCTCGACAA 3801

1908 GGCGAACCTGCTTACGCTCAGTgCCCCTGAGATGACGGTGCTGGTAGGTG 1957
     ||||||||||||||||||||| ||||||||||||||||||||||||||||
3802 GGCGAACCTGCTTACGCTCAGTGCCCCTGAGATGACGGTGCTGGTAGGTG 3851

1958 GCCTGCGCGTCCTCGG.GCAAACTACAAGcGCTTACCGCTGGGCGTgTTC 2006
     |||||||||||||||| ||||||||||||| ||||||||||||||| |||
3852 GCCTGCGCGTCCTCGGCGCAAACTACAAGCGCTTACCGCTGGGCGTGTTC 3901
```

FIG. 1C

```
2007 ACCGAGGCCTCCGAGTCACTGACCAACGACTTCTTCGTGAACCTGCTCGA 2056
     ||||||||||||||||||||||||||||||||||||||||||||||||||
3902 ACCGAGGCCTCCGAGTCACTGACCAACGACTTCTTCGTGAACCTGCTCGA 3951

2057 CATGGGTATCACCTGGGAGCCCTCGCCAGCAGATGaCGGgACCTACCAGG 2106
     ||||||||||||||||||||||||||||||||||||||||||||||||||
3952 CATGGGTATCACCTGGGAGCCCTCGCCAGCAGATGACGGGACCTACCAGG 4001

2107 GcAAGGATGGCAGTgGCAAGGTGAAGTGGACCGGcAGCCGCGTGGACCTG 2156
     ||||||||||||||||||||||||||||||||||||||||||||||||||
4002 GCAAGGATGGCAGTGGCAAGGTGAAGTGGACCGGCAGCCGCGTGGACCTG 4051

2157 gTCTTCGGgtCCAACTCGGAGTTGCGGGCGCTTGTCGAGGTCTATGGCGC 2206
     |||||||||||||||||||||||||||||||||||||||||||||| ||||
4052 GTCTTCGGGTCCAACTCGGAGTTGCGGGCGCTTGTCGAGGTCTAT.GCGC 4100

2207 CGATGACGC.GCAGCCGAAGTTCGTGCAGGACTTCGTCGCTGCCTGGgAC 2255
     |||||||||  ||||  ||||||||||||   |   ||||||||| ||||||
4101 CGATGACGCGGCAGGCGAAGTTCGTGACAGGATTCGTCGCTGCGTGGGAC 4150

▼
2256 AAGGTGATGAACCTCGACAGGTTCGACGTgCGCTGATTCG 2295
     ||||||||||||||||||||||||||||||||||||||||
4151 AAGGTGATGAACCTCGACAGGTTCGACGTGCGCTGATTCG 4190
```

FIG. 1D

```
N            11          21          31          41
  1 VPEQHPPITE  TTTGAASNGC  PVVGHMKYPV  EGGGNQDWWP  NRLNLKVLHQ

N            61          71          81          91
 51 NPAVADPMGA  AFDYAAEVAT  IDVDALTRDI  EEVMTTSQPW  WPADYGHYGP

N            11          21          31          41
101 LFIRMAWHAA  GTYRIHDGRG  GAGGGMQRFA  PLNSWPDNAS  LDKARRLLWP

N            61          71          81          91
151 VKKKYGKKLS  WADLIVFAGN  CALESMGFKT  FGFGFGRVDQ  WEPDEVYWGK

N            11          21          31          41
201 EATWLGDERY  SGKRDLENPL  AAVQMGLIYV  NPEGPNGNPD  PMAAAVDIRE

N            61          71          81          91
251 TFRRMAMNDV  ETAALIVGGH  TFGKTHGAGP  ADLVGPEPEA  APLEQMGLGW

N            11          21          31          41
301 KSSYGTGTGK  DAITSGIEVV  WTNTPTKWDN  SFLEILYGYE  WELTKSPAGA

N            61          71          81          91
351 WQYTAKDGAG  AGTIPDPFGG  PGRSPTMLAT  DLSLRVDPIY  ERITRRWLEH

N            11          21          31          41
401 PEELADEFAK  AWYKLIHRDM  GPVARYLGPL  VPKQTLLWQD  PVPAVSHDLV

N            61          71          81          91
451 GEAEIASLKS  QIRASGLTVS  QLVSTAWAAA  SSFRGSDKRG  GANGGRIRLQ

N            11          21          31          41
501 PQVGWEVNDP  DGDLRKVIRT  LEEIQESFNS  AAPGNIKVSF  ADLVVLGGCA

N            61          71          81          91
551 AIEKAAKAAG  HNITVPFTPG  RTDASQEQTD  VESFAVLEPK  ADGFRNYLGK

N            11          21          31          41
601 GNPLPAEYML  LDKANLLTLS  APEMTVLVGG  LRVLGANYKR  LPLGVFTEAS

N            61          71          81          91
651 ESLTNDFFVN  LLDMGITWEP  SPADDGTYQG  KDGSGKVKWT  GSRVDLVFGS

N            11          21          31          41
701 NSELRALVEV  YGADDAQPKF  VQDFVAAWDK  VMNLDRFDVR  &
```

FIG. 2

```
            10                  30                  50
CGATATCCGACACTTCGCGATCACATCCGTGATCACAGCCCGATAACACCAACTCCTGGA 70                  90                 110
     AGGAATGCTGTGCCCGAGCAACACCCACCCATTACAGAAACCACCACCGGAGCCGCTAGC
1             V  P  E  Q  H  P  P  I  T  E  T  T  T  G  A  A  S         17

130                 150                 170
     AACGGCTGTCCCGTCGTGGGTCATATGAAATACCCCGTCGAGGGCGGCGGAAACCAGGAC
18    N  G  C  P  V  V  G  H  M  K  Y  P  V  E  G  G  G  N  Q  D         37

190                 210                 230
     TGGTGGCCCAACCGGCTCAATCTGAAGGTACTGCACCAAAACCCGGCCGTCGCTGACCCG
38    W  W  P  N  R  L  N  L  K  V  L  H  Q  N  P  A  V  A  D  P         57

250                 270                 290
     ATGGGTGCGGCGTTCGACTATGCCGCGGAGGTCGCGACCATCGACGTTGACGCCCTGACG
58    M  G  A  A  F  D  Y  A  A  E  V  A  T  I  D  V  D  A  L  T         77

310                 330                 350
     CGGGACATCGAGGAAGTGATGACCACCTCGCAGCCGTGGTGGCCCGCCGACTACGGCCAC
78    R  D  I  E  E  V  M  T  T  S  Q  P  W  W  P  A  D  Y  G  H         97

370                 390                 410
     TACGGGCCGCTGTTTATCCGGATGGCGTGGCACGCTGCCGGCACCTACCGCATCCACGAC
98    Y  G  P  L  F  I  R  M  A  W  H  A  A  G  T  Y  R  I  H  D        117

430                 450                 470
     GGCCGCGGCGGCGCCGGGGGCGGCATGCAGCGGTTCGCGCCGCTTAACAGCTGGCCCGAC
118   G  R  G  G  A  G  G  G  M  Q  R  F  A  P  L  N  S  W  P  D        137

490                 510                 530
     AACGCCAGCTTGGACAAGGCGCGCCGGCTGCTGTGGCCGGTCAAGAAGAAGTACGGCAAG
138   N  A  S  L  D  K  A  R  R  L  L  W  P  V  K  K  K  Y  G  K        157

550                 570                 590
     AAGCTCTCATGGGCGGACCTGATTGTTTTCGCCGGCAACTGCGCGCTGGAATCGATGGGC
158   K  L  S  W  A  D  L  I  V  F  A  G  N  C  A  L  E  S  M  G        177

610                 630                 650
     TTCAAGACGTTCGGGTTCGGCTTCGGCCGGGTCGACCAGTGGGAGCCCGATGAGGTCTAT
178   F  K  T  F  G  F  G  F  G  R  V  D  Q  W  E  P  D  E  V  Y        197

670                 690                 710
     TGGGGCAAGGAAGCCACCTGGCTCGGCGATGAGCGTTACAGCGGTAAGCGGGATCTGGAG
198   W  G  K  E  A  T  W  L  G  D  E  R  Y  S  G  K  R  D  L  E        217

730                 750                 770
     AACCCGCTGGCCGCGGTGCAGATGGGGCTGATCTACGTGAACCCGGAGGGGCCGAACGGC
218   N  P  L  A  A  V  Q  M  G  L  I  Y  V  N  P  E  G  P  N  G        237

790                 810                 830
     AACCCGGACCCCATGGCCGCGGCGGTCGACATTCGCGAGACGTTTCGGCGCATGGCCATG
238   N  P  D  P  M  A  A  A  V  D  I  R  E  T  F  R  R  M  A  M        257

850                 870                 890
     AACGACGTCGAAACAGCGGCGCTGATCGTCGGCGGTCACACTTTCGGTAAGACCCATGGC
258   N  D  V  E  T  A  A  L  I  V  G  G  H  T  F  G  K  T  H  G        277
```

FIG. 7A

```
                    910               930                950
          GCCGGCCCGGCCGATCTGGTCGGCCCCGAACCCGAGGCTGCTCCGCTGGAGCAGATGGGC
278       A  G  P  A  D  L  V  G  P  E  P  E  A  A  P  L  E  Q  M  G       297

970               990                1010
          TTGGGCTGGAAGAGCTCGTATGGCACCGGAACCGGTAAGGACGCGATCACCAGCGGCATC
298       L  G  W  K  S  S  Y  G  T  G  T  G  K  D  A  I  T  S  G  I       317

1030              1050               1070
          GAGGTCGTATGGACGAACACCCCGACGAAATGGGACAACAGTTTCCTCGAGATCCTGTAC
318       E  V  V  W  T  N  T  P  T  K  W  D  N  S  F  L  E  I  L  Y       337

1090              1110               1130
          GGCTACGAGTGGGAGCTGACGAAGAGCCCTGCTGGCGCTTGGCAATACACCGCCAAGGAC
338       G  Y  E  W  E  L  T  K  S  P  A  G  A  W  Q  Y  T  A  K  D       357

1150              1170               1190
          GGCGCCGGTGCCGGCACCATCCCGGACCCGTTCGGCGGGCCAGGGCGCTCCCCGACGATG
358       G  A  G  A  G  T  I  P  D  P  F  G  G  P  G  R  S  P  T  M       377

1210              1230               1250
          CTGGCCACTGACCTCTCGCTGCGGGTGGATCCGATCTATGAGCGGATCACGCGTCGCTGG
378       L  A  T  D  L  S  L  R  V  D  P  I  Y  E  R  I  T  R  R  W       397

1270              1290               1310
          CTGGAACACCCCGAGGAATTGGCCGACGAGTTCGCCAAGGCCTGGTACAAGCTGATCCAC
398       L  E  H  P  E  E  L  A  D  E  F  A  K  A  W  Y  K  L  I  H       417

1330              1350               1370
          CGAGACATGGGTCCCGTTGCGAGATACCTTGGGCCGCTGGTCCCCAAGCAGACCCTGCTG
418       R  D  M  G  P  V  A  R  Y  L  G  P  L  V  P  K  Q  T  L  L       437

1390              1410               1430
          TGGCAGGATCCGGTCCCTGCGGTCAGCCACGACCTCGTCGGCGAAGCCGAGATTGCCAGC
438       W  Q  D  P  V  P  A  V  S  H  D  L  V  G  E  A  E  I  A  S       457

1450              1470               1490
          CTTAAGAGCCAGATCCGGGCATCGGGATTGACTGTCTCACAGCTAGTTTCGACCGCATGG
458       L  K  S  Q  I  R  A  S  G  L  T  V  S  Q  L  V  S  T  A  W       477

1510              1530               1550
          GCGGCGGCGTCGTCGTTCCGTGGTAGCGACAAGCGCGGCGGCGCCAACGGTGGTCGCATC
478       A  A  A  S  S  F  R  G  S  D  K  R  G  G  A  N  G  G  R  I       497

1570              1590               1610
          CGCCTGCAGCCACAAGTCGGGTGGGAGGTCAACGACCCCGACGGGGATCTGCGCAAGGTC
498       R  L  Q  P  Q  V  G  W  E  V  N  D  P  D  G  D  L  R  K  V       517

1630              1650               1670
          ATTCGCACCCTGGAAGAGATCCAGGAGTCATTCAACTCCGCGGCGCCGGGGAACATCAAA
518       I  R  T  L  E  E  I  Q  E  S  F  N  S  A  A  P  G  N  I  K       537

1690              1710               1730
          GTGTCCTTCGCCGACCTCGTCGTGCTCGGTGGCTGTGCCGCCATAGAGAAAGCAGCAAAG
538       V  S  F  A  D  L  V  V  L  G  G  C  A  A  I  E  K  A  A  K       557
```

FIG. 7B

```
            1750                1770                1790
      GCGGCTGGCCACAACATCACGGTGCCCTTCACCCCGGGCCGCACGGATGCGTCGCAGGAA
558   A  A  G  H  N  I  T  V  P  F  T  P  G  R  T  D  A  S  Q  E    577

1810                1830                1850
      CAAACCGACGTGGAATCCTTTGCCGTGCTGGAGCCCAAGGCAGATGGCTTCCGAAACTAC
578   Q  T  D  V  E  S  F  A  V  L  E  P  K  A  D  G  F  R  N  Y    597

1870                1890                1910
      CTCGGAAAGGGCAACCCGTTGCCGGCCGAGTACATGCTGCTCGACAAGGCGAACCTGCTT
598   L  G  K  G  N  P  L  P  A  E  Y  M  L  L  D  K  A  N  L  L    617

1930                1950                1970
      ACGCTCAGTGCCCCTGAGATGACGGTGCTGGTAGGTGGCCTGCGCGTCCTCGGCGCAAAC
618   T  L  S  A  P  E  M  T  V  L  V  G  G  L  R  V  L  G  A  N    637

1990                2010                2030
      TACAAGCGCTTACCGCTGGGCGTGTTCACCGAGGCCTCCGAGTCACTGACCAACGACTTC
638   Y  K  R  L  P  L  G  V  F  T  E  A  S  E  S  L  T  N  D  F    657

2050                2070                2090
      TTCGTGAACCTGCTCGACATGGGTATCACCTGGGAGCCCTCGCCAGCAGATGACGGGACC
658   F  V  N  L  L  D  M  G  I  T  W  E  P  S  P  A  D  D  G  T    677

2110                2130                2150
      TACCAGGGCAAGGATGGCAGTGGCAAGGTGAAGTGGACCGGCAGCCGCGTGGACCTGGTC
678   Y  Q  G  K  D  G  S  G  K  V  K  W  T  G  S  R  V  D  L  V    697

2170                2190                2210
      TTCGGGTCCAACTCGGAGTTGCGGGCGCTTGTCGAGGTCTATGGCGCCGATGACGCGCAG
698   F  G  S  N  S  E  L  R  A  L  V  E  V  Y  G  A  D  D  A  Q    717

2230                2250                2270
      CCGAAGTTCGTGCAGGACTTCGTCGCTGCCTGGGACAAGGTGATGAACCTCGACAGGTTC
718   P  K  F  V  Q  D  F  V  A  A  W  D  K  V  M  N  L  D  R  F    737

2290                2310                2330
      GACGTGCGCTGATTCGGGTTGATCGGCCCTGCCCGCCGATCAACCACAACC
738   D  V  R  *                                              740
```

FIG. 7C

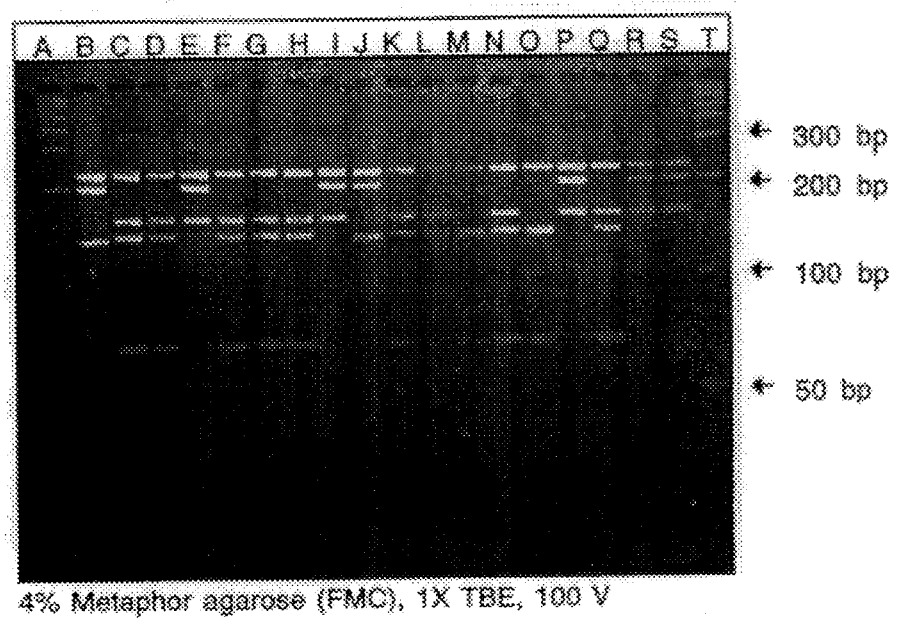
RFLP analysis of M. tuberculosis katG mutations in codons 315 and 463.
4% Metaphor agarose (FMC), 1X TBE, 100 V
A&T = MW markers
B-S = MspI digests of PCR products (katG 904-1523)
| | |
|---|---|
| C,D,F,G,H,K,L,N,Q | wild genotype at codons 315 and 463 |
| M,O | RFLP indicating a mutation at codon 315 |
| E,I,P | RFLP indicating a mutation at codon 463 |
| B,J | RFLP indicating mutations at codons 315 and 463 |

DETECTION OF ISONIAZID RESISTANT STRAINS OF *M. TUBERCULOSIS*

This is a continuation-in-part application of U.S. patent application Ser. No. 08/228,662 filed Apr. 18, 1994, which is incorporated herein by reference.

BACKGROUND OF THE INVENTION

Despite more than a century of research since the discovery of *Mycobacterium tuberculosis*, the aetiological agent of tuberculosis, this disease remains one of the major causes of human morbidity and mortality. There are an estimated 3 million deaths annually attributable to tuberculosis (see, D. Snider, *Rev. Inf. Dis.*, S335 (1989)), and although the majority of these are in developing countries, the disease is assuming renewed importance in the West due to the increasing number of homeless people and the impact the AIDS epidemic (see, R. E. Chaisson et at., *Am. Res. Resp. Dis.*, 23, 56 (1987); D. E. Snider, Jr. et al., *New Engl. J. Med.*, 326, 703 (1992); M. A. Fischl et al., *Ann. Int. Med.*, 117, 177 (1992) and ibid. at 184.

Isonicotinic acid hydrazide or isoniazid (INH) has been used in the treatment of tuberculosis for the last forty years due to its exquisite potency against the members of the "tuberculosis" groups—*Mycobacterium tuberculosis, M. bovis* and *M. africanum* (G. Middlebrook, *Am. Rev. Tuberc.*, 69, 471(1952) and J. Youatt, *Am. Rev. Resp. Dis.*, 99, 729 (1969)). Neither the precise target of the drug, nor its made of action are known, but INH treatment results in the perturbation of several metabolic pathways of the bacterium. However, shortly after its introduction, INH-resistant isolates of *Mycobacterium tuberculosis* emerged. See M. L. Pearson et al., *Ann. Int. Med.*, 117, 191 (1992) and S. W. Dooley et al., *Ann. Int. Med.*, 117, 257 (1992).

Several investigators have associated the toxicity of INH for mycobacteria with endogenous catalase activity. See, for example, "Isonicotinic acid hydrazide," in F. E. Hahn, *Mechanism of Action of Antibacterial Agents*, Springer-Verlag (1979) at pages 98–119. This relationship was strengthened by a recent report by Ying Zhang and colleagues in *Nature*, 358, 591 (1992) which described the restoration of INH susceptibility in an INH resistant *Mycobacterium smegmatis* strain after transformation using the catalase-peroxide (katG) gene from an INH sensitive *M. tuberculosis* strain. In a follow-up study, Zhang and colleagues in *Molec. Microbiol.*, 8, 521 (1993) demonstrated the restoration of INH susceptibility in INH resistant *M. tuberculosis* strains after transformation by the functional katG gene. As reported by B. Heym et al., *J. Bacteriol.*, 175, 4255 (1993), the katG gene encodes for a 80,000-dalton protein.

A significant problem in control of multiple drug resistant tuberculosis (MDR-TB) epidemics has been the delay in the detection of drug resistance. Currently laboratory methods used to identify *M. tuberculosis* drug resistance require weeks to months for results. The rapid detection of *M. tuberculosis* directly from clinical samples has been possible recently by virtue of the availability of polymerase chain reaction (PCR) and the recognition of diagnostic sequences amplified by the appropriate primers. The ability to conduct PCR analyses depends on having a high enough gene or gene product concentration so that the molecular tools work efficiently even when the organism numbers are low. Thus, the most efficient molecular assays used to detect *M. tuberculosis* depend on the IS6110 insertion sequence (about 10 copies) or the 16S ribosomal RNA (thousands of copies). See, respectively, K. D. Eisenach et al., *J. Infect. Dis.*, 61,997 (1990) and N. Miller et al., *Abstracts ASM*, Atlanta, Ga. (1993) at page 177. Recently, B. Heym et al., (PCT WO 93122454) disclose the use of polymerase chain reaction to amplify portions of the katG gene of putative resistant strains. The PCR products were evaluated by single-strand conformation polymorphism (SSCP) analysis, wherein abnormal strand motility on a gel is associated with mutational events in the gene. For example, in five strains, a single base difference was found in a 200 bp sequence, a G to T transversion at position 3360. This difference would result in the substitution of Arg-461 by Leu. However, carrying out SSCP on a given clinical sample can be a laborious procedure that requires sequencing to confirm whether mutations or deletions predictive of drug resistance are in fact present in the target gene.

There is a continuing need in the art to develop a simple test permitting the rapid identification of INH-resistant strains of *M. tuberculosis.*

SUMMARY OF THE INVENTION

The present invention provides a method to rapidly identify strains of *M. tuberculosis* which are resistant to isoniazid (INH). The method is based on our discovery that certain mutations in the katG gene of *M. tuberculosis* which confer INH resistance coincidentally result in the addition or deletion of restriction sites, which are recognized by various restriction enzymes. For example, the wild-type (WT) katG gene of *M. tuberculosis* contains an NciI-MspI restriction site spanning codon 463, which site is absent in the corresponding codon 463 in a number of INH resistant strains due to a single base mutation in that codon. An NciI-MspI restriction site is a site cleaved by both NciI and MspI. This site is represented by the nucleotide sequence CCGGG (see Table 1).

Alternatively, or in addition, some INH resistant strains have a single base mutation in codon 315 in the katG gene that produces a new MspI restriction site associated with the corresponding codon 315 in the INH resistant strain. Some INH resistant strains have a single base mutation at codon 337 that results in the deletion of a RsaI restriction site otherwise present at the corresponding position in the WT gene; and some have a single base mutation at codon 264 that eliminates a CfoI restriction site. These mutations may be present singly or in combination in INH resistant *M. tuberculosis* strains.

When used in reference to nucleotide position, codon position or restriction site position, the term "corresponding" is defined to mean the same absolute location on two different *M. tuberculosis* katG genes, wherein absolute location is defined by the numbering system used in FIG. 7 (SEQ ID NO: 20). For example, a wild-type codon 463 represented by CGG at nucleotide positions 1456–1458 on a wild-type katG gene of *M. tuberculosis* and a mutant codon 463 represented by CTG at the same nucleotide positions 1456–1458 on a katG gene of an INH resistant strain of *M. tuberculosis* are considered to be corresponding codons.

The determination of whether one or more of these identifying mutations in the katG gene are present in a strain of *M. tuberculosis* can be made by employing the techniques of restriction fragment length polymorphism (RFLP) analysis. Therefore, in an embodiment directed to the identification of a mutation in codon 463 that is associated with INH resistance, the present assay comprises the steps of:

(a) amplifying a portion of the katG gene of an *M. tuberculosis* isolate to yield a detectable amount of DNA comprising the nucleotide position occupied by base 1457 of the *M. tuberculosis* katG gene consensus sequence depicted in
FIG. 7 (SEQ ID NO: 20); and (b) determining whether an NciI-MspI restriction site is absent
in codon 463 of said katG gene, wherein said absence is indicative of an INH resistant strain of *M. tuberculosis*.

The RFLP technique involves cleaving the DNA with a restriction endonuclease which cleaves at an NciI-MspI restriction site to yield at least one DNA fragment and determining whether the number and location of the fragments is indicative of the absence of an NciI-MspI restriction site in codon 463 of said katG gene, wherein said absence is indicative of an INH resistant strain of *M. tuberculosis*, preferably by employing the techniques of gel electrophoresis.

If the amplified DNA of step (a) contains no NciI-MspI restriction sites, then the DNA fragment yielded in step (b) will be identical to the amplified DNA of step (a). This can occur where the portion of the katG gene amplified in step (a) is from an INH resistant strain of *M. tuberculosis* having a mutation in codon 463 that removes the NciI-MspI restriction site spanning that codon in the wild-type katG gene, and having no other additional NciI-MspI restriction sites.

In order for the amplified DNA to yield a meaningful RFLP pattern, the portion of the katG gene amplified in step (a) will be of sufficient length to produce fragments of sufficient length to visualize using gel electrophoresis. In the above-described embodiment, for example, the portion amplified will contain a sufficient number of bases to either side (5' or 3') of codon 463 such that cleavage at a site spanning that codon will yield fragments that can be visualized using gel electrophoresis.

In another embodiment of the invention directed to the additional identification of a mutation in codon 315 associated with INH resistance, the amplified DNA of step (a) further comprises at least one MspI restriction site and the nucleotide position occupied by base 1013 (FIG. 7, SEQ ID NO:20), and the determination made in step (b) further includes whether an MspI restriction site associated with codon 315 is present, wherein said presence is indicative of an INH resistant strain. For example, RFLP can also be employed to determine whether the number and location of the fragments is indicative of the codon 315 MspI restriction site. Preferably, the portion of the katG locus which is amplified is a minor portion of the entire katG gene, i.e., less than 1500 base pair, more preferably less than 1000 base pair, and is isolated and amplified by polymerase chain reaction, as described hereinbelow. The term "location" refers to the Rf (relative electrophoretic mobility) of a given fragment on the gel.

The pattern of fragments produced on a gel by electrophoresis of a restriction digest of an amplified portion of the katG gene of an *M. tuberculosis* strain of interest, such as an INH resistant strain, is preferably compared to the pattern produced in a digest of an equivalent portion of the katG gene of a wild-type (WT) control strain of *M. tuberculosis*, which strain is INH sensitive. The term "equivalent" is defined herein to mean that any two portions of the katG gene would comprise the same number and location of restriction sites being analyzed (e.g., sites recognized by CfoI, RsaI, MspI, and/or NciI) if the portions both were selected from a portion of the DNA of SEQ ID NO: 20 (i.e., if there were no mutations altering the number of restriction sites of the type being analyzed), and that the portions do not differ in size before cleavage to the extent that the number of fragments obtained cannot be compared following side-by-side gel electrophoresis and visualization of the resultant fragments, as described hereinbelow. For example, the control katG DNA can correspond to an equivalent portion of SEQ ID NO:20 (FIG. 7, upper sequence) comprising one or more of the codons of interest (e.g., codons 315 or 463) and their associated restriction sites. As discussed below, such a portion of DNA can be derived from strain H37Rv MC. A positive control corresponding to DNA fragments derived from a known INH resistant strain may also be used.

In the embodiment of the assay of the invention directed to the determination of the presence or absence of a NciI-MspI restriction site associated with codon 463, gel electrophoresis is employed to compare the number and location of the DNA fragments to the number and location of DNA fragments derived from cleavage of DNA derived from an equivalent portion of the katG gene wherein the NciI-MspI restriction site at codon 463 is determination of the absence of the restriction site at codon 463 in the katG gene is indicative of an INH resistant strain of *M. tuberculosis*. Preferably, the control DNA sequence of the portion of the katG gene wherein the codon 463 restriction site is present corresponds to a portion of SEQ ID NO:20 (FIG. 7, upper sequence). For example, the control DNA may contain five NciI-MspI restriction sites in each DNA molecule prior to cleavage, and the DNA of step (a), which is derived from an INH resistant strain, may contain four NciI-MspI restriction sites in each DNA molecule prior to cleavage. The assay also preferably includes positive control DNA fragments derived from an INH resistant strain which does not include the codon 463 NciI-MspI restriction site in the katG gene.

The present invention also provides oligonucleotides and subunits thereof useful in pairs as primers to initiate the polymerase chain reaction (PCR). Subunits of at least seven bases in length are preferred. PCR is useful both to amplify katG DNA so as to prepare both the target DNA of step (a) of the present process, as well as the DNA which is used to prepare the control digest.

The present invention also provides isolated, purified DNA represented by the consensus sequence derived for the *M. tuberculosis* katG gene. This DNA was found to occur in nature as the katG gene of *M. tuberculosis* strain H37Rv MC, as maintained at the Mayo Clinic, and is also referred to as the wild-type (WT) DNA. The present invention also includes isolated, purified DNA encoding the consensus amino acid sequence encoded by the consensus wild-type katG DNA, as well as DNA sequences that differ in sequence but which also encode this amino acid sequence (a consensus catalase peroxidase polypeptide) and can be employed to provide the isolated, purified polypeptide represented by the consensus amino acid sequence, which polypeptide is also provided by the invention.

The polypeptide of the invention can be prepared by expression in transformed host cells, such as bacteria, yeast, plant, or insect cells transformed with the DNA sequences of the present invention, operatively linked to regulatory regions functional in the transformed host cells. The polypeptide can be used as a standard *M. tuberculosis* catalase peroxidase, to correlate enzymatic activity (relative level, loss and restoration), with INH modification and degradation and drug resistance in *M. tuberculosis*.

The present invention also provides a kit comprising, separately packaged in association:

(a) a pair of oligonucleotide primers selected so as to amplify a portion of the DNA of the *M. tuberculosis* katG gene comprising base 1457 in codon 463 or base 1013 in codon 315, as depicted in FIG. 7 (SEQ ID NO:20); and (b) an amount of a restriction endonuclease such as MspI, effective to cleave the amplified portion of said DNA at a restriction site comprising said base 1457 or said base 1013.

The present kits will also preferably comprise instruction means for carrying out the present assay, i.e., a printed package insert, tag or label, or an audio or video tape. The present kits will also preferably comprise a control DNA digest prepared by amplifying a portion of the consensus DNA of SEQ ID NO:20 (FIG. 7), that is equivalent to the portion defined and amplified by the pair of primers, followed by digestion of the DNA with a suitable restriction endonuclease such as MspI.

The present invention is exemplified by the use of NciI, MspI, CfoI, and RsaI digestions, with the use of MspI digestion being preferred; however, any restriction endonuclease having a restriction site spanning all or a portion of codon 463, codon 315, codon 337, or codon 264, which portion contains the site of the single base mutation associated with INH resistance as identified in Table 2, may be used, as desired. For example, the restriction endonucleases listed in Table 1 can be employed. Particularly preferred are restriction endonucleases having a restriction site that contains the position occupied by base 1457 in codon 463, or base 1013 in codon 315, as depicted in FIG. 7 (SEQ ID NO:20).

TABLE 1

| M. tuberculosis* katG gene Specificity | Restriction Site | Restriction Enzyme |
|---|---|---|
| Cuts 264-A (sensitive) | C/CGC | AciI[a] |
| | GC/NGC[b] | BsoFI, Fnu4HI, Bsp6I, BssFI, BssXI, Cac824I, CcoP215I, CcoP216I, FbrI, ItaI, Uur960I |
| | R/GCGCY[c] | Bsp143II, HaeII, Bme14ZI, BsmHI, Bst1473II, Bst16I, Btu34II, HinHI, LpnI, NgoI |
| | G/CGC | CfoI, HhaI, BcaI, CcoP95I, Csp1470I, FnuDIII, Hin6I, Hin7I, HinGUI, HinPII, IlinSII, IlinS2I, MnnIV, SciNI |
| Cuts 264-T (resistant) | GACGCNNNNN/NNNNN (SEQ ID NO: 22) | HgaI |
| Cuts 337-Y (resistant) | GT/AC | RsaI, AfaI, Asp16HI, Asp17HI, Asp18HI, Asp29HI, CcoP73I, Csp6I, CviQI, CviRII |
| Cuts 337-C | GC/NGC | BsoFI, Fnu1HI, Bsp6I, BssFI, |

TABLE 1-continued

| M. tuberculosis* katG gene Specificity | Restriction Site | Restriction Enzyme |
|---|---|---|
| (resistant) | | BssFI, BssXI, Cac824I, CcoP215I, CcoP216I, FbrI, ItaI, Uur960I |
| | C/CGC | AciI[a] |
| Cuts 315-S (sensitive) | C/CGC | AciI[a] |
| | GC/NGC | BsoFI, Fnu4HI, Bsp6I, BssFI, BssXI, Cac824I, CcoP215I, CcoP216I, FbrI, ItaI, Uur960I |
| | CMG/CKG[d] | MspAII, NspBII |
| Cuts 315-T (resistant) | R/CCGGY[e] | BsrFI, Cfr10I, Bco118I, Bse118I, Bsp21I, BssAI |
| | C/CGG | MspI, Bsu1192I, BsuFI, FinI, HapII, Hin2I, Hin5I, HpaII, MniII, MnoI, MspI, Pde137I, Pme35I, SecII, SfaGUI, Sth134I, Uba1128I, Uba1141I, Uba1267I, Uba1338I, Uba1355I, Uba1439I |
| Cuts 463-R (sensitive) | CC/SGG[f] | NciI, BcnI, AhaI |
| | C/CGG | MspI, Bsu1192I, BsuFI, FinI, HapII, Hin2I, Hin5I, HpaII, MniII, MnoI, MspI, Pde137I, Pme35I, SecII, SfaGUI, Sth134I, Uba1128I, Uba1141I, Uba1267I, Uba1338I, Uba1355I, Uba1439I |
| Cuts 463-L (resistant) | CAG/NNN/CTG | AlwNI |
| | CC/WGG[g] | BstNI, BstOI, MvaI |
| | /CCWGG | EcoRII |

[a]AciI cleaves the complementary strand of the katG gene;
[b]N = C or G or A or T;
[c]R = A or G;
[d]M = A or C, K = G or T;
[e]Y = C or T;
[f]S = C or G;
[g]W = A or T.

TABLE 2[a]

| | | | | |
|---|---|---|---|---|
| 264-A (sensitive)[b] | (SEQ ID NO: 8) | 847 | GTC GAA ACA GCG GCG CTG ATC GTC GGC | 873 |
| 264-T (resistant) | (SEQ ID NO: 9) | | GTC GAA ACA GCG ACG CTG ATC GTC GGC | |
| 337-Y (sensitive)[c] | (SEQ ID NO: 10) | 1066 | CTC GAG ATC CTG TACGGC TAC GAG TGG | 1092 |
| 337-C (resistant) | (SEQ ID NO: 11) | | CTC GAG ATC CTG TGC GGC TAC GAG TGG | |
| 315-S (sensitive)[d] | (SEQ ID NO: 12) | 1000 | GAC GCG ATC ACC AGC GGC ATC GAG GTC | 1026 |
| 315-T (resistant) | (SEQ ID NO: 13) | | GAC GCG ATC ACC ACC GGC ATC GAG GTC | |
| 463-R (sensitive)[e] | (SEQ ID NO: 14) | 1444 | AAG AGC CAG ATC CGG GCA TCG GGA TTG | 1470 |
| 463-L (resistant) | (SEQ ID NO: 15) | | AAG AGC CAG ATC CTG GCA TCG GGA TTG | |

[a]The underlined codons represent the sites where the indicated single base mutations confer INH resistance. The bold bases indicate restriction sites as follows: G/CGC for CfoI in 264-A (sensitive); GT/AC for RsaI in 337-Y (sensitive); C/CGG for MspI in 315-T (resistant) and 463-R (sensitive). For ease of reference, the partial sequences shown in this table include the 12 bases to either side of the affected codon; the numbering system is the same as used for the wild-type consensus sequence in FIGS. 1 and 7. The full sequence of bases to either side of the affected codon is shown in FIG. 7. In each of the sensitive/resistant pairs shown in this table, the upper sequence is the consensus, wild-type sequence (INH-sensitive) and the lower sequence is the mutant (INH-resistant) sequence.
[b]codon 264 GCG = ala (A) ACG = thr (T)
[c]codon 337 TAC = tyr (Y) TGC = cys (C)
[d]codon 315 AGC = ser (S) ACC = thr (T)
[e]codon 463 CGG = arg (R) CTG = leu (L)

BRIEF DESCRIPTION OF THE DRAWINGS

FIG. 1, panels A–D, depicts the consensus, wild-type DNA sequence of the *M. tuberculosis* katG gene as the upper of the pair of sequences (61–2295) (SEQ ID NO:1). This DNA sequence data has been submitted to Gen Bank and has been assigned accession number UO6262. The lower of the pair of sequences depicts nucleotide sequence 1970–4190 of the KpnI fragment bearing the katG gene as depicted in FIG. 6 of Institute Pasteur et al. (published PCT application WO 93/22454). This sequence (SEQ ID NO:2) has been deposited in the EMBL data library under accession number X68081 (Gen Bank X68081. gb_ba). Dots (.) above the sequence mark every tenth base. The upper sequence is in lower case in areas where variation in the sequence among isolates described hereinbelow and the consensus sequence was found. The arrow before position 70 and after position 2291 of the upper sequence indicate the coding sequence of the katG gene.

FIG. 2 depicts the katG amino acid consensus sequence derived from 15 strains of *M. tuberculosis* (SEQ ID NO:7).

FIG. 3 schematically depicts the NciI restriction sites for the part B amplicon of katG. The (*) depicts the site of the Arg→Leu mutation which is found in some INH resistant *M. tuberculosis* strains.

FIG. 4 depicts the results of a gel electrophoresis of the NciI digest of the part B amplicon of 14 strains of *M. tuberculosis* (1–14).

FIG. 5 schematically depicts MspI and RsaI restriction sites and resulting RFLP fragments for a portion of the *M. tuberculosis* katG gene. For MspI, restriction maps for wild-type (W+), single (315 Ser→Thr or 463 Arg→Leu) mutants and the double (315 Ser→Thr and 463 Arg→Leu) mutant are shown. For RsaI, restriction maps for wild-type (W+) and the 337 W→C mutant are shown.

FIG. 6 schematically depicts CfoI restriction sites and resulting RFLP fragments for a portion of the *M. tuberculosis* katG gene. Restriction maps for wild-type (W+) and the 264 A→T mutant are shown.

FIG. 7, panels A–C, depict as the upper of the pair of sequences the consensus, wild-type DNA sequence of the *M. tuberculosis* katG gene (SEQ ID NO:20), and as the lower of the pair of sequences the amino acid consensus sequence encoded thereby (SEQ ID NO:21). This information is updated from that presented in FIGS. 1 (SEQ ID NO:1) and 2 (SEQ ID NO:7) and the numbering system is as used therein. The amino acid and nucleotide sequences are arranged in this figure so as to facilitate convenient determination of which codons encode which amino acid in the polypeptide sequence.

FIG. 8 depicts the RFLP patterns produced by an MspI restriction digest of an amplified portion of the DNA of the katG genes of wild-type and mutant strains of *M. tuberculosis*, wherein the mutant DNA contains mutations at either codon 315 or codon 463, or both.

FIG. 9 depicts the RFLP patterns produced by an RsaI restriction digest of an amplified portion of the DNA of the katG genes of wild-type and mutant strains of *M. tuberculosis*, wherein the mutant DNA contain a mutation at codon 337.

FIG. 10 depicts the RFLP patterns produced by a CfoI restriction digest of an amplified portion of the DNA of the katG genes of wild-type and mutant strains of *M. tuberculosis*, wherein the mutant DNA contains a mutation codon 264.

DETAILED DESCRIPTION OF THE INVENTION

Wild type strains of *M. tuberculosis* are highly susceptible to isoniazid (INH) with minimum inhibitory INH concentration (MIC or $IC_{min}$) ≦0.02 μg/ml, and a susceptible strain is considered to be one with an $IC_{min}$<1.0 μg/ml. At the Mayo Clinic, Rochester, Minn., clinical strains of *M. tuberculosis* (including MDR-TB strains) were identified which exhibit intermediate to high level resistance to INH ($IC_{min}$ range 1.0 to >32 μg/ml). Many of these strains, especially those highly resistant to INH (≧4.0 μg/ml), exhibited diminished catalase activity as assessed by a semiquantitative technique. The mean semiquantitative catalase was 16.5 mm for 6/15 strains with INH $IC_{min}$<1.0 μg/ml and 13.3 mm for 9/15 strains with $IC_{min}$≧1.0 μg/ml.

To develop the present assay, it was first necessary to determine whether some *M. tuberculosis* strains have decreased INH sensitivity as a result of katG gene mutations. Therefore, the nucleic acid sequences of the katG genes for both INH sensitive ($IC_{min}$<1.0 μg/ml) and INH resistant ($IC_{min}$≧1.0 μg/ml) *M. tuberculosis* strains were determined. From the DNA sequencing data generated, a katG consensus sequence was derived, and katG sequences from all 15 *M. tuberculosis* strains (INH sensitive and INH resistant) were compared to the consensus sequence to determine katG deviations.

Five of nine INH resistant strains (INH $IC_{min} \geq 1.0$ µg/ml) had one or more missense mutations; one had a nonsense mutation; one had an 8 base pair deletion; and two had no mutations in the coding sequences. All of the five strains with missense mutations had a common G to T transversion at base 1457 in codon 463 (bases 1456–1458) causing replacement of arginine with leucine and loss of an NciI-MspI restriction site. Two of those having mutations at codon 463 also showed a G to C transversion at base 1013 in codon 315 (bases 1012–1014) causing replacement of serine with threonine. A third contained a G to A transversion at base 859 in codon 264 (bases 859–861) resulting in the replacement of alanine by threonine, and a fourth contained an A to G transversion at base 1079 in codon 337 (bases 1078–1080), causing tyrosine to be replaced by cysteine. The numbering system is shown in FIG. 1 (SEQ ID NO:1). The affected codons and portions of the DNA sequences on either side are shown for both INH sensitive and INH resistant strains in Table 2.

Figure 3:
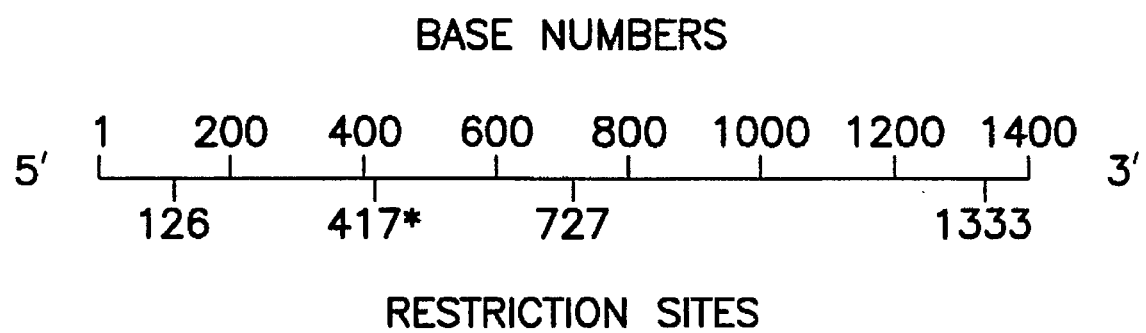

Six INH sensitive strains (INH $IC_{min}<1.0$ µg/ml) were also sequenced and found to have from none to 5 amino acid differences with the consensus sequence of all 15 strains, but none of the mutations affected codons 463, 315, 264, or 337 or their overlapping restriction sites. Restriction analysis of a total of 32 sensitive and 43 resistant strains revealed a common restriction fragment length polymorphism (RFLP) in nearly half (19) of the 43 of INH resistant strains, but only one of the INH sensitive strains. Specifically, 44% of the INH resistant had lost the NciI-MspI restriction site at the locus of codon 463 while only 1 of 32 sensitive strains had this restriction polymorphism.

Subsequently, the frequency of codon 463 (R→L) and codon 315 (S→T) mutations in 97 M. tuberculosis clinical isolates was determined. These isolates were obtained from patients treated at Mayo Clinic and samples referred from other health care institutions. Restriction fragment length polymorphism (RFLP) analysis using the MspI restriction enzyme, which cleaves at a site spanning the consensus codon 463 site and at a site comprising a portion of the mutant codon 315 site on the katG gene of M. tuberculosis, was performed on amplified DNA from 97 clinical isolates. Comparison of the resulting RFLP patterns and $IC_{min}$ for isoniazid revealed that of the 90 INH-resistant strains, approximately 10% had both mutations, 20% had the 315 S→T mutation only, and 26% had the 463 R→L mutation only. Thus, 51 of the 90 resistant strains were identified by RFLP as having mutations at codons 463, 315 or both, resulting in a detection of over 50% of the resistant strains by this molecular method in a single experiment. Only one of the seven INH sensitive strains was found to have the 463 R→L mutation, and none of the INH sensitive strains had the 315 S→T mutation. Greater INH resistance (>4.0 µg, INH/ml) is associated with the 315 S→T mutation, but not if the 463 R→L mutation is also present.

These results indicate that two mutations, arginine→leucine in codon 463 and serine→leucine in codon 315 of the M. tuberculosis catalase-peroxidase (katG) gene occur in a significant fraction of INH resistant M. tuberculosis strains (INH $IC_{min} \geq 1.0$ µg/ml). Furthermore, these single base mutations can be determined using a rapid relatively simple method, i.e., PCR amplification, digestion and monitoring for a loss of an NciI and/or an MspI restriction site at codon 463, and the addition of an MspI restriction site at codon 315, by RFLP, as described in detail hereinbelow. Other restriction endonucleases can be used to determine whether or not these single base mutations exist in a katG gene of interest, as long as the restriction site cleaved by the restriction endonucleases contains the affected base, such that the endonuclease cleaves the wild-type sequence but not the corresponding mutant sequence, or vice versa. Although in a preferred embodiment of the invention, the number and location of the fragments is determined by gel electrophoresis, the presence or absence in the digest of a fragment comprising the indicated restriction sites can be determined by other methods known to the art, including immunoassays (dot blots and reverse dot blots), DNA probes, microtiter well capture and the like.

The present invention will be further described by reference to the following detailed examples. The 58 clinical strains of *Mycobacterium tuberculosis* used in Examples 1 and 2 were obtained from the Mycobacteriology Laboratory at the Mayo Clinic, Rochester, Minn., and the 17 *M. tuberculosis* DNA preparations were obtained from the GWL Hansen's Disease Center, Louisiana State University, Baton Rouge, La. The strain designated H37Rv MC has been maintained at the Mayo Clinic for over 50 years, and therefore was isolated before INH became available as a treatment modality for tuberculosis (circa 1952). H37Rv was deposited in the American Type Tissue Collection, Rockville, Md. in 1937 by A. Karlson of the Mayo Clinic under the accession number ATCC 25618, and has been freely available to the scientific community since. An apparent variant of this strain is disclosed in PCT WO 93/22454 (SEQ ID NO:2, herein). The ATCC strains 27294 and 25618 were recovered from the same patient in 1905 and 1934, respectively. All clinical *M. tuberculosis* strains were confirmed as *M. tuberculosis* using routine identification techniques described by J. A. Washington, "Mycobacteria and Norcardia," in: *Laboratory Procedures in Clinical Microbiology*, 2d ed., Springer-Verlag, N.Y. (1985) at pages 379–417.

For the 15 *M. tuberculosis* strains for which complete katG DNA sequencing was performed, susceptibility testing was done at the Mayo Clinic using Middlebrook 7H11 agar (DiMed, Inc., St. Paul, Minn. 55113) and the 1% proportion method described in *Manual of Clinical Microbiology*, 5th ed., A. Balows et al., eds., *Amer. Soc. Microbiol.* (1991) at pages 1138–52. The same method was used at the Mayo Clinic to determine susceptibility for an additional 43 *M. tuberculosis* strains for which restriction fragment length polymorphisms (RFLP) were determined. Isoniazid concentrations tested using this method included: 0.12, 0.25, 1.0, 2, 4, 8, 16, 32 μg/ml for the 15 strains sequenced and 1.0 and 4.0 μg/ml for the remaining 45 strains. Isoniazid resistance was defined as a maximum inhibitory concentration ($IC_{min}$) $\geqq 1.0$ μg/ml. Susceptibility testing was performed elsewhere for an additional 17 *M. tuberculosis* strains for which DNA lysates were provided by Diana L. Williams, Baton Rouge, La. These strains were of diverse geographical origin. 10 of these 17 strains, originated from Japan. The remaining 7 *M. tuberculosis* INH resistant strains included multiple drug resistant strains from recent multiple drug resistant tuberculosis (MDR-TB) nosocomial epidemics in New York, N.Y. and Newark, N.J. All were INH resistant ($IC_{min} \geqq 1.0$ μg/ml), and had resistance to at least one other drug. For all strains provided by Williams, the 1% direct proportion method was used, but the concentration of INH tested, and the media used varied as to site.

To conduct a semiquantitative test of catalase activity, *M. tuberculosis* strains were propagated on Lowenstein-Jensen media deeps contained in 20×150 mm screw-capped tubes. One ml of a 30% hydrogen peroxide (EM, Science, Gibbstown, N.Y. 08027) and 10% Tween 80 (Aldrich Chemical Co., Milwaukee, Wis. 53233) solution mixed in a

EXAMPLE 1.

DNA Isolation and Polymerase Chain Reaction.

A. DNA Isolation.

For *M. tuberculosis* strains obtained from Mayo Clinic samples, DNA was extracted from cells using phenol (Boehringer Mannheim, Indianapolis, Ind. 46250-0414) and TE (1.0M Tris HC1 pH 8.0, 0.1M EDTA, Sigma, St. Louis, Mo. 63778) in a ratio of 600 μl:400 μl and 0.1 mm zirconium beads (Biospec Products, Bartlesville, Okla. 74005). The mixture was processed in a mini-bead beater for 30 seconds and allowed to stand for an additional 15 minutes. Following a brief centrifugation to sediment the zinconium beads, DNA in the supernatant was extracted using the IsoQuick kit (MicroProbe Corp., Garden Grove, Calif. 92641).

B. PCR Using Primer Pairs A1–A4 and B1–B2.

The DNA sequence for katG (EMBL no. X6808124) employed to design primers is depicted in FIG. 1(A–D), lower strand. The PCR method of R. K. Saiki et al., *Science*, 239, 487 (1988) was used to amplify the katG gene (ca. 2220 base pairs) in two segments which were designated A and B. Genomic DNA preparations (2 μl) were used with primers A1 (5' TCGGACCATAACGGCTTCCTGTTGGACGAG 3') (SEQ ID NO:3) and A4 (5' AATCTGCTTCGCCGAC-GAGGTCGTGCTGAC 3') (SEQ ID NO:4) or B1 (5' CAC-CCCGACGAAATGGGACAACAGTTTCCT 3') (SEQ ID NO:5) and B2 (5' GGGTCTGACAAATCGCGC-CGGGCAAACACC 3') (SEQ ID NO:6).

The PCR mixture (50 μl) contained 10 mM TRIS, pH 8.3, 50 mM KCl, 1.5 mM MgCl$_2$, 0.2 mM each of dATP, dTTP, dGTP, dCTP, 1μM of each primer pair, 10% glycerol, 1.25 units/50 μl AmpliTaq DNA polymerase (Perkin Elmer Cetus). The mixture was overlaid with mineral oil and subjected to 4 min at 95° C. followed by 50 cycles of 1 min at 94° C. and 2 min at 74° C. A 1495 base pair product from the first half of katG was generated from the A1–A4 primers and 1435 base pair product was generated with the B 1–B2 primer pair.

EXAMPLE 2.

DNA Sequencing and Homology Analysis.

The polymerase chain reaction (PCR) products were prepared for sequencing using the Magic™ PCR Preps DNA Purification System (Promega Corp., Madison, Wis. 53711). The DNA sequences were determined in both directions using the Taq dye-deoxy terminator cycle sequencing kit and 373A DNA sequencer (Applied Biosystems, Foster City, Calif. 94404) using a series of internal sequencing primers which provided appropriate coverage of katG.

The sequence data were analyzed using version 7 of the Genetics Computer Group sequence analysis software, as disclosed by J. Devereux et al., *Nucl. Acids Res.*, 12, 387 (1984). From the 15 *M. tuberculosis* DNA sequences, a consensus sequence was derived to which all *M. tuberculosis* strains were compared. This consensus sequence is depicted in FIG. 1 (A–D) (SEQ ID NO:1) as the upper strand, and is compared to the sequence for katG (EMBL no. X6808124), depicted as the lower strand. The two sequences have 98.6% identity, as determined by the GCG program BESTFIT. The DNA sequence data has been submitted to Gen Bank and can be referenced by the accession numbers U06262 (H37Rv MC), U06258 (ATCC 25618), U06259 (ATCC 27294), U06260 (G6108), U06261 (H35827), U06270 (L6627-92), U06271 (L68372), U06264 (L11150), U06268 (L24204), U06269 (L33308), U06265 (L16980), U06266 (L1781), U06272 (TMC306), U06263 (L10373), and U06267 (L23261). An updated, more complete and accurate *M. tuberculosis* katG gene sequence is presented in FIG. 7 (A–C) (SEQ ID NO:20).

The DNA data was then translated, aligned for comparison and a consensus amino acid sequence was generated (FIG. 2) (SEQ ID NO:7). The consensus amino acid sequence (SEQ ID NO:21) generated from the DNA of SEQ ID NO:20 is also presented in FIG. 7.

In general, the overall sequence agreement between INH sensitive and resistant strains was very high; the only deviations are those shown in Table 3.

TABLE 3

Analysis of Catalase-Peroxidase (katG) Gene in *M. tuberculosis* Strains

| Strain | INH MIC$^A$ (μg/ml) INH | Catalase | Amino Acid Codon$^b$ | | | | | |
|---|---|---|---|---|---|---|---|---|
| | | | 2 | 10 | 17 | 90 | 224 | 243 |
| H37Rv MC | <0.12 | 20 | | | | | | |
| ATCC 25618 | <0.12 | 12 | | | | | | |
| ATCC 27294 | 0.12 | 28 | P–S | | S–N | | Q–E | A–S |
| G6108 | <0.12 | 12 | | | | | | |
| H35827 | 0.25 | 14 | | | | | | |
| L6627-92 | 0.5 | 13 | | | | | | |
| L68372 | 1 | 8 | | | | | | |
| L11150 | 8 | 28 | | | | | | |
| L24204 | 8 | 36 | | | | | | |
| L33308 | 8 | 15 | | | | | | |
| L16980 | 16 | 15 | | | | | | |
| L1781 | 32 | 5 | | | | | | |
| TMC 306 | >32 | 5 | | | | | W*$^c$ | |
| L10373 | >32 | 5 | | 8 bpd$^d$ | | | | |
| L23261 | >32 | 5 | | | | | | |
| | | Consensus | P | | S | W | Q | A |

TABLE 3-continued

Analysis of Catalase-Peroxidase (katG) Gene in M. tuberculosis Strains

| Strain | INH MIC[A] (μg/ml) INH | Catalase | Amino Acid (Codon)[b] | | | | | | | |
|---|---|---|---|---|---|---|---|---|---|---|
| | | | 264 | 315 | 337 | 424 | 463 | 505 | 550 | 609 |
| H37Rv MC | <0.12 | 20 | | | | | | | | |
| ATCC 25618 | <0.12 | 12 | | | | | | | | |
| ATCC 27294 | 0.12 | 28 | | | | | | | A–D | |
| G6108 | <0.12 | 12 | | | | | | | | M–I |
| H35827 | 0.25 | 14 | | | | | | | | |
| L6627-92 | 0.5 | 13 | | | | | | | | |
| L68372 | 1 | 8 | | | Y–C | | R–L | | | |
| L11150 | 8 | 28 | | | | | | | | |
| L24204 | 8 | 36 | | S–T | | | R–L | | | |
| L33308 | 8 | 15 | | | | | | | | |
| L16980 | 16 | 15 | | S–T | | | R–L | | | |
| L1781 | 32 | 5 | A–T | | | | R–L | | | |
| TMC 306 | >32 | 5 | | | | | | | | |
| L10373 | >32 | 5 | | | | A–V | | | A–D | |
| L23261 | >32 | 5 | | | | | R–L | W–R | | M–I |
| | | Consensus | A | S | Y | A | R | W | A | M |

[A]MIC denotes Maximum Inhibitory Concentration, INH denotes isoniazid
[b]A denotes alanine, C cysteine, D aspartic acid, E glutamic acid, F phenylalanine, G glycine, I isoleucine, K lysine, L leucine, M methionine, N asparagine, P proline, Q glutamine, R arginine S serine, T threonine, V valine, W tryptophan, Y tryosine, B bpd B base pair deletion
[c]TGG→TGA (W→stop codon)
[d]8 base pair deletion corresponding to wild type coordinates 98–105 creates a new TAG stop codon beginning 11 bp from coordinate 97.

The data in Table 3 show that six strains, H37Rv MC, ATCC 25618, H35827, L6627-92, L11150, and L33308, are completely homologous to the consensus at the indicated sites. Four are INH sensitive (INH $IC_{min}$<1.0 μg/ml) and two are INH resistant ($IC_{min}$>1.0 μg/ml). All other strains listed in Table 3 had 1 to 5 differences with the consensus and there was no strong correlation between the number of differences and INH sensitivity.

In the group of INH resistant strains, the most frequent change observed was the conversion of arginine at codon 463 to leucine. This was detected in five of nine isolates examined. There was not a consistent correlation between the loss of catalase activity and INH resistance since strains L11150 and L24204 had high levels of enzymatic activity, yet were INH resistant. Moreover, several other INH resistant strains showed catalase activity near the mean activity (16.5 mm) of the sensitive strains. Two other isolates had lost the ability to make normal katG gene product due either to an eight bp deletion (L10373, semiquantitative catalase, 3mm) or a nonsense mutation (TMC 306, semiquantitative catalase 5 mm). It was not possible to determine if, or how, any of the deviations from the consensus reported in Table 3 affect catalase activity or cause INH resistance. However, the change at codon 463 is frequent enough that is indicative of resistance.

The DNA sequence analysis indicated that the codon 463 occurs in the context of an NciI-MspI restriction site (both enzymes recognize the same site). Thus, when in the wild type sequence depicted in FIG. 1 at bases 1455–1458, CCGGG, is changed to CCTGG, it is no longer recognized (or cleaved) by either of these enzymes. The 1435 bp amplicon produced from the half of katG gene containing codon 463 normally has five NciI-MspI restriction sites whereas the codon altered strains have only four sites, as shown in FIG. 3. The loss of the site in question causes a unique restriction fragment length polymorphism (RFLP), which can be readily adapted to assay for resistant strains, as described in Example 3, below.

EXAMPLE 3.

RFLP Analysis: MspI-NciI site in Codon 463

For restriction fragment length polymorphism (RFLP) analysis, a 1435 base pair amplimer (produced using the B 1–B2 primers) representing the 3' half of the katG gene was generated using PCR and then digested with NciI or MspI (Sigma Chemical Co., St. Louis, Mo. 63178). The gene fragments were analyzed with agarose gel electrophoresis using 2% Metaphor agarose (FMC BioProducts, Richland, Me. 04811). The gel was stained with ethidium bromide and photographed. The investigator who performed all restriction digests and electrophoresis was blinded as to the INH $IC_{min}$ results.

Figure 4:
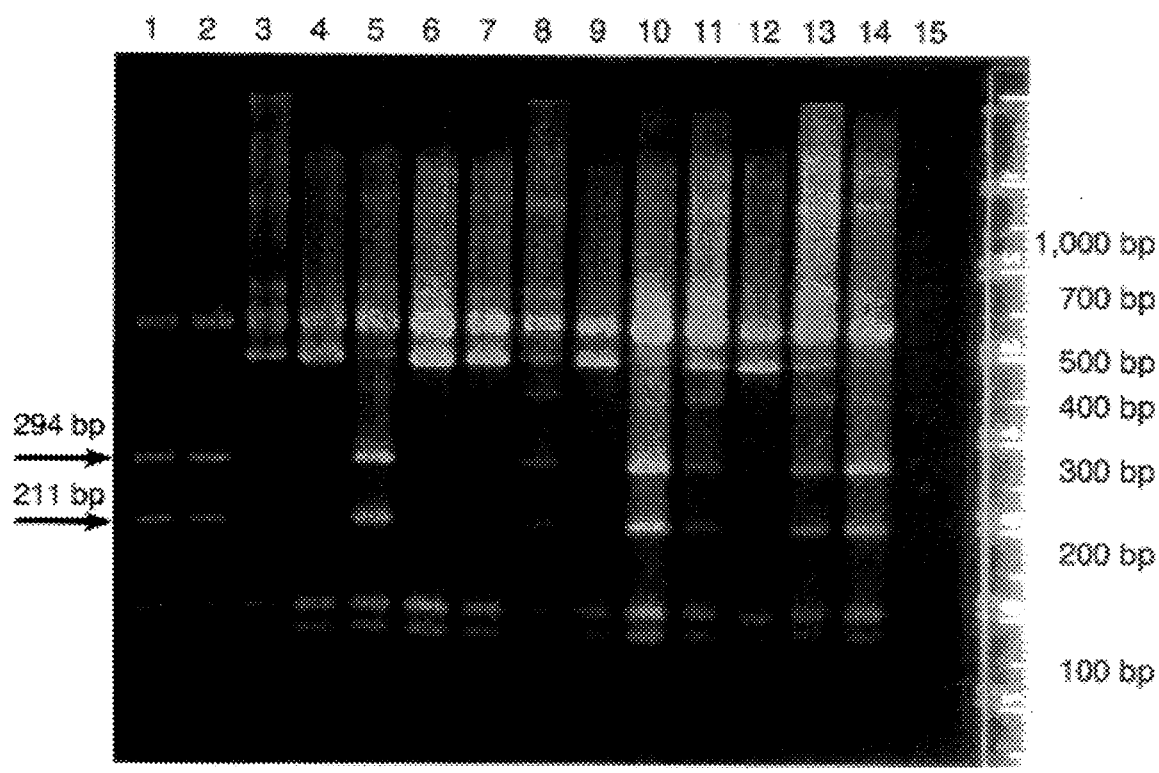
Figure 5:
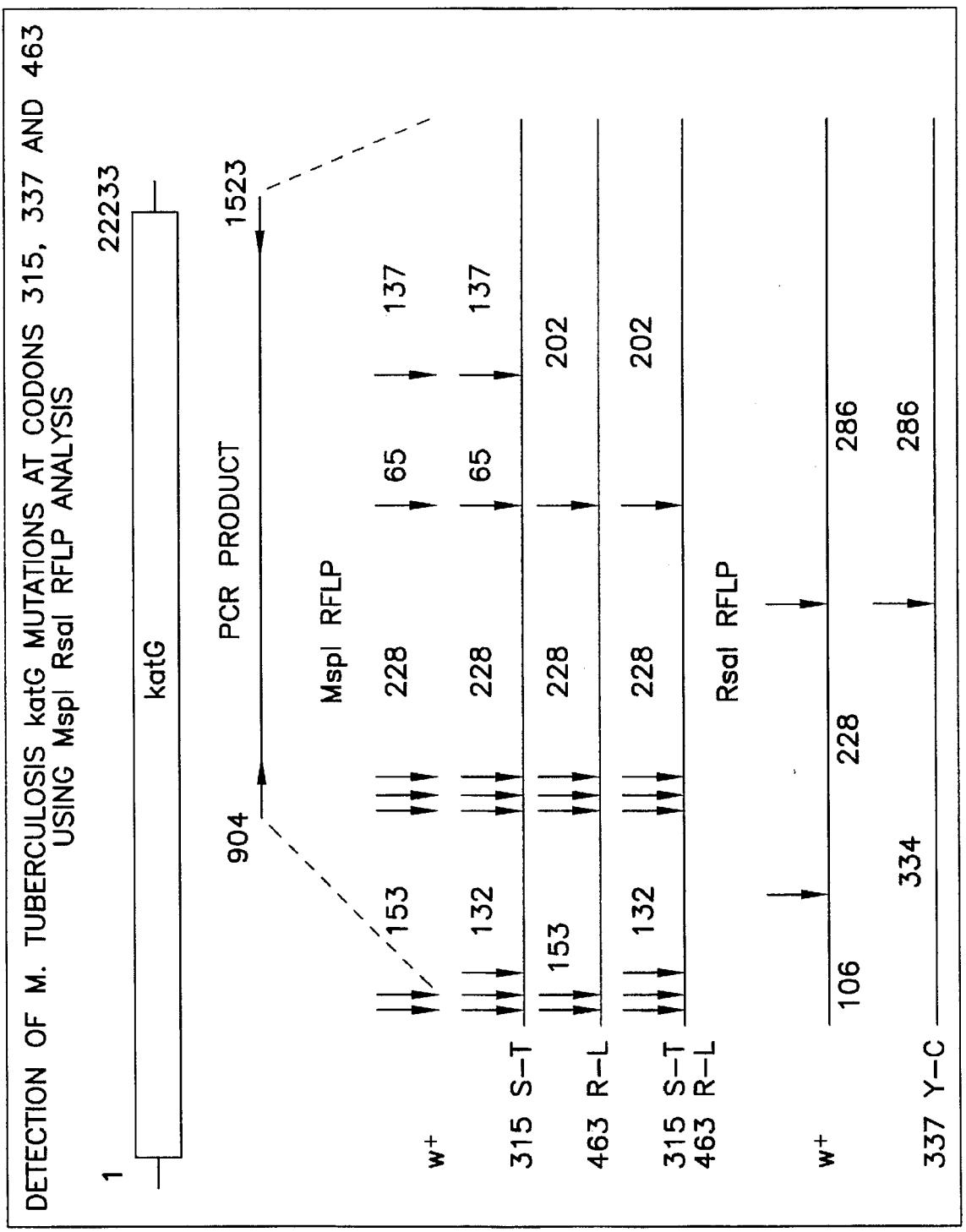
Figure 6:
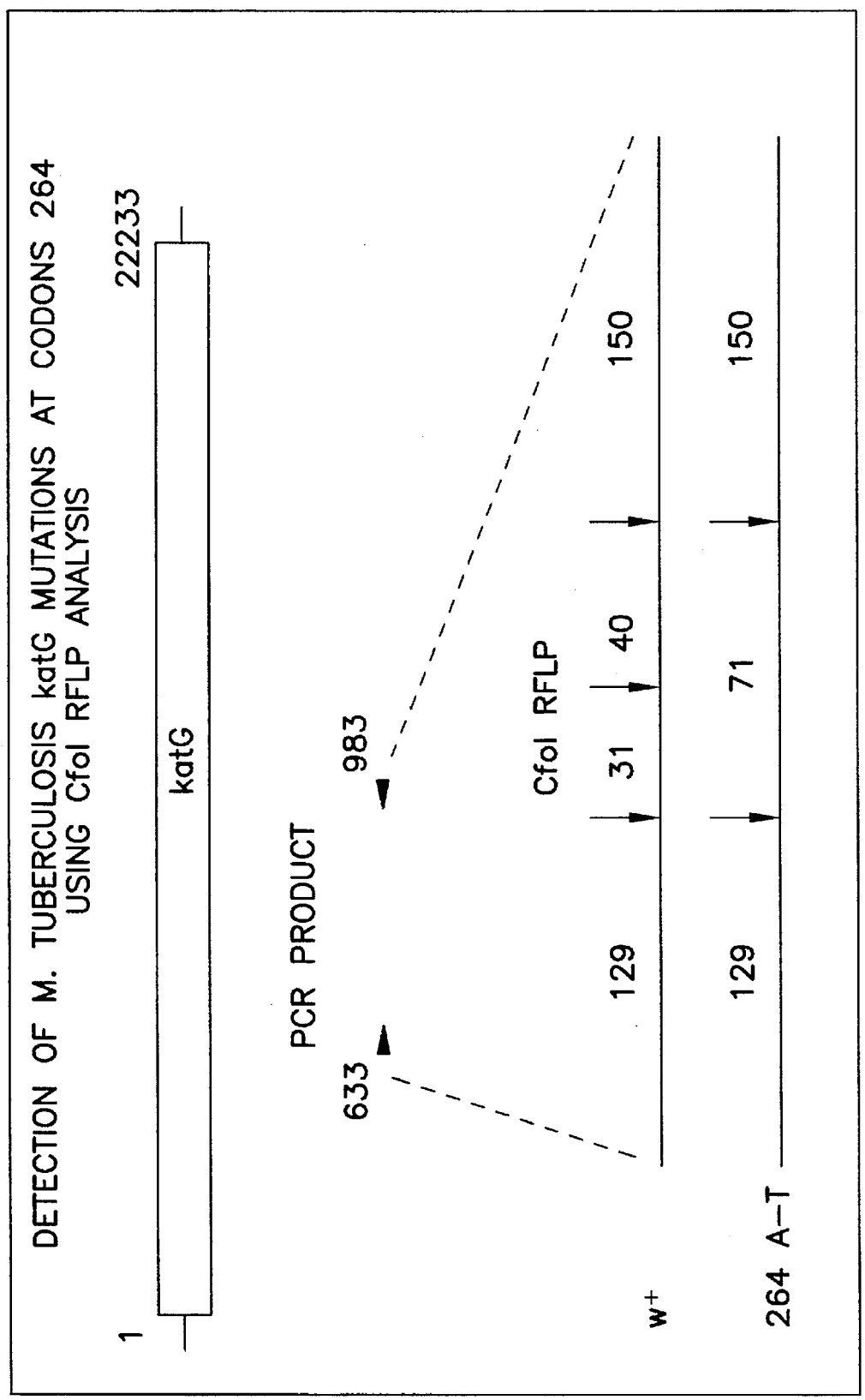
Figure 9:
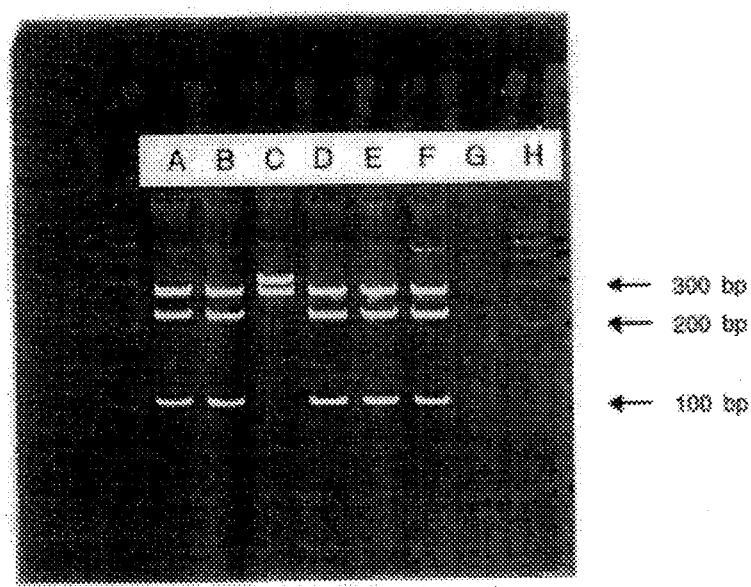

The results of this experiment are depicted in FIG. 4, wherein Lane 1 denotes strain H37Rv MC, $IC_{min}$=<0.12 μg/mL; (2) L6627-92, 0.5 μg/mL; (3) L68372, 1.0 μg/ml; (4) L16980, 16 μg/mL; (5) L39791, 16 μg/mL; (6) L1781, 32 μg/mL; (7) L9118, 4 μg/mL; (8) L11150, 8 μg/mL; (9) L24204, 8 μg/mL; (10) L68858, <0.12 μg/mL; (11) 1115A<0.12 μg/mL; (12) L23261, >32 μg/mL; (13) 1341, >32 μg/mL; (14) M10838, >32 μg/mL; (15) molecular weight standard: PCR markers (United States Biochemical Corp., Cleveland, Ohio 44122). The digests obtained from resistant strains can be readily visually detected and differentiated from digests from susceptible strains.

Subsequently, a total of 75 M. tuberculosis strains (including the 15 strains sequenced) were analyzed for their loss of the appropriate restriction site. Of these strains, 32 were INH sensitive and 43 were INH resistant. The data showed that 19 (44%) of the 43 resistant strains had lost the expected restriction site in codon 463. One of the 33 (2.9%) sensitive strains had lost this restriction sites as well. None of the six sensitive strains listed in Table 3 lost this site.

15

EXAMPLE 4.

Determination of the Presence or Absence of Mutations at Codons 264, 315, 337 or 463 in the *M. tuberculosis* katG Gene A. Materials.

Primer pairs used for polymerase chain reaction were katG904katG1523 (nucleotide sequences 5' AGC TCG TAT GGC ACC GGA AC 3' (SEQ ID NO:16) and 5' TTG ACC TCC CAC CCG ACT TG 3' (SEQ ID NO:17)) and katG633katG983 (nucleotide sequences 5' CGG TAA GCG GGA TCT GGA GA 3' (SEQ ID NO:18) and 5' CAT TTC GTC GGG GTG TTC GT 3' (SEQ ID NO:19)). Subunits thereof that hybridize to the amplified DNA under the conditions described hereinbelow may also be used.

Polyacrylamide was obtained from National Diagnostics, Tris Borate EDTA solution (6X, cat. no. T6400), magnesium chloride, and dithiothreitol (DTT) from Sigma Chemical Company (St. Louis, Mo.), TEMED (cat. no. 161-0800) and ethidium bromide (EtBr) from Biorad, ammonium persulfate from Intermountain Sci., and nucleotides (dATP, dGTP, dCTP and dTTP, 100mM solutions) from Boehringer Mannheim Biochemicals. dUTP was obtained from Pharmacia. AmpErase™ uracil-N-glycosylase (UNG) and AmpliTaq™ were obtained from Perkin Elmer.

Restriction endonucleases were obtained as follows: MspI from Sigma (cat. no. R-4506) 10 u/μl with blue palette buffer; RsaI from New England Biochemical (cat. no. 167S) 10 u/μl with NEB buffer 1; and CfoI from Promega (cat. no. R624) 10 u/μl with buffer B.

100 mM nucleotide concentrates obtained from Boehringer Mannheim Biochemicals were used to make the dNTP stock solution, which was 1.25 mM in each nucleotide. Specifically, 10 μl each of dATP, dGTP, dCTP, and dTTP concentrates were added to 760 μl water. dNTP(U) stock solution, also 1.25 mM in each nucleotide, was made from the same 100 mM dATP, dGTP and dCTP concentrates, and 100 mM dUTP concentrate from Pharmacia. Ten μl of each of the four concentrates was added to 760 μl water to make the stock solution.

10X PCR buffer consisted of 100 mM Tris, pH 8.3, 500 mM KCl, and 15 mM $MgCl_2$. PCR mix "A" consisted of 1X PCR buffer, 200 μM each dATP, dGTP, dCTP, and dUTP, 1 μM each katG904 (SEQ ID NO: 16) and katG1523 (SEQ ID NO: 17) primers, 10% glycerol, 10 units/m/ AmpErase™UNG, and 0.025 units/μl AmpliTaq. PCR mix B consisted of 1X PCR buffer, 200 μM each dATP, dGTP, dCTP, and dTTP, 1 μM each katG904 (SEQ ID NO: 16) and katG1523 (SEQ ID NO: 17) primers, 10% glycerol, and 0.025 units/μl AmpliTaq. PCR mix "C" consisted of 1X PCR buffer, 200 μM each dATP, dGTP, dCTP, and dUTP, 1 μM each katG633 (SEQ ID NO: 18) and katG983 (SEQ ID NO: 19) primers, 10% glycerol, 10 units/ml AmpErase™UNG, and 0.025 units/μl AmpliTaq.

Gel loading solution (Blue Juice) was obtained from Sigma (cat. no. G-2526). Gels were photographed on a UV transilluminator (UVP) with Polaroid 667 black and white film (3¼×4¼ inch) through an orange filter.

DNA extracts (target DNA) were prepared as described in Example I(A).

B. MspI RFLP Analysis.

PCR was performed by adding 2 μl of DNA extract to 48 μl PCR mix "A." Each reaction was covered with 2 drops of mineral oil. Temperature was cycled (Perkin Elmer DNA Thermo Cycler model 480) for 1 cycle of (5'—37°; 5'—95°) and 40 cycles of (1'—94°; 0.5'—60°; 0.75'—72°) and a 72° soak. MspI(10 u/μl) was diluted 1:10 in 100 mM $MgCl_2$. The amplified DNA (base pairs 904 through 1523) of a wild-type katG gene contains 7 MspI restriction sites (FIG. 5); of the 8 fragments produced in an MspI restriction digest, 4 are of sufficient length to be visualized using gel electrophoresis (see FIG. 5 for a restriction map). Diluted MspI (1 μl ) was mixed with 9 μl of the PCR reaction mixture containing the amplified DNA. The digest was incubated at 37° C. for 2 hours, then heated to 65° C. for 10 minutes. Subsequently, 10 μl of the digest plus 4 μl blue juice was electrophoresed on 6% polyacrylamide for 0.4 hour at 200 V. The gel was stained in EtBr (0.5 mg/ml 1XTBE) for 5 minutes and photographed.

Results are shown in FIG. 8. Lanes C, D, F, G, H, K, L, N, and Q show the wild-type genotype at codons 315 (AGC) and 463 (CGG) evidenced by 4 restriction of sufficient length to be visualized using gel electrophoresis (228, 153, 137, and 65 base pairs, respectively, see FIG. 5). Lanes M and 0 show an RFLP indicating a mutation at codon 315 that adds a new MspI restriction site, causing the 153 base pair fragment to be shortened to 132 base pair and become difficult to resolve from the 137 base pair fragment. The resulting 3 fragment pattern (65, 132/137 and 228 base pair) is indicative of an INH resistant strain. Lanes E, I and P show an RFLP indicating a mutation at codon 315 that eliminates an MspI restriction site, evidenced by the 3 visible fragments produced by cleavage versus the 4 produced by the wild-type genotype. The resulting 3 fragment pattern (153, 202, and 228 base pair) is indicative of an INH resistant strain. Lanes B and J show an RFLP indicating mutations at both codon 315 and codon 463. The resulting gain and loss of MspI restriction sites produces a distinctive 3 fragment RFLP pattern (132, 202 and 228 base pair) indicative of an INH resistant strain (see FIG. 5 for a restriction map).

C. RsaI RFLP Analysis.

PCR was performed by adding 2 μl of DNA extract to 48 μl PCR mix "B." Each reaction was covered with 2 drops of mineral oil. Temperature was cycled (Perkin Elmer DNA Thermo Cycler model 480) for 1 cycle of 2 minutes at 94° and 40 cycles of (1'—94°; 0.5'—60°; 0.75'—72°) and a 4° soak. RsaI (10 u/μl) was diluted 1:20 in 100 mM $MgCl_2$/100 mM dithiothreitol. The amplified DNA (bases 904 through 1523) of a wild-type katG gene contains 2 RsaI restriction sites. Diluted RsaI (2 μl) was placed on top of the PCR reaction mixture (on the oil) and centrifuged at about 12,000× g for 10 seconds to drop the RsaI enzyme into the mixture containing the amplified DNA. The resulting mixture was incubated overnight (15–20 hours) at 37°, after which 10 μl of the digest plus 1 μl blue juice was electrophoresed on 6% polyacrylamide for 0.4 hour at 200 V. The gel was stained in EtBr (0.5 mg/ml 1XTBE) for 5 minutes and photographed.

Results are shown in FIG. 9. Lanes A, B, D, E, and F show the wild-type genotype at codon 337 (TAC), evidenced by three restriction fragments produced by cleavage at two sites. Lane C shows an RFLP indicating a mutation at codon 337 that eliminates one of the RsaI restriction sites. The resulting two fragment pattern has been observed in an INH resistant strain.

D. CfoI RFLP Analysis.

PCR was performed by adding 2 μl of DNA extract to 48 μl PCR mix "C." Each reaction was covered with 2 drops of mineral oil. Temperature was cycled (Perkin Elmer DNA Thermo Cycler model 480) for 1 cycle of (5'—37°; 5'—95°) and 40 cycles of (1'—94°; 0.5'—60°; 0.75'—72°) and a 72° soak. The amplified DNA (bases 633 through 983) of a wild-type katG gene contains 3 CfoI restriction sites. CfoI (10 u/μl) was diluted 1:5 in 100 mM $MgCl_2$. Diluted CfoI (1 μl) was mixed with 9 μl of the PCR reaction mixture containing the amplified DNA. The digest was incubated at 37° for 2 hours, then heated to 65° C. for 10 minutes. Subsequently, 10 μl of the digest plus 4 μl blue juice was electrophoresed on 6% polyacrylamide for 0.4 hour at 200

V. The gel was stained in EtBr (0.5 mg/ml 1XTBE) for 5 minutes and photographed.

Figure 10:
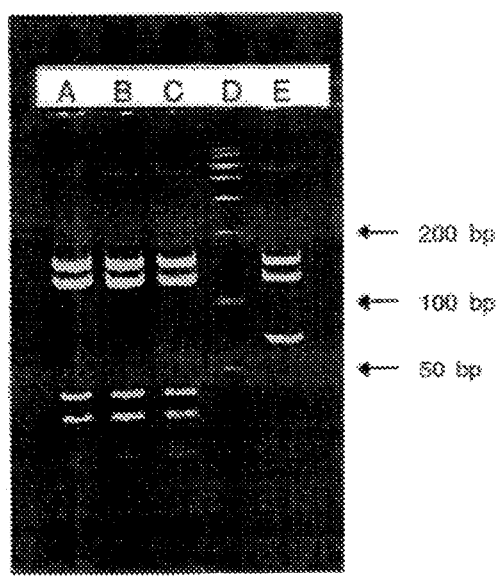

Results are shown in FIG. 10. Lanes A–C show the wild-type genotype at codon 264 (GCG), evidenced by 4 restriction fragments produced by cleavage at three sites. Lane E shows an RFLP indicating a mutation at codon 264 that eliminates one of the CfoI restriction sites. The resulting three fragment pattern has been observed in an INH resistant strain All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for determining the susceptibility of a strain of M. tuberculosis to isoniazid comprising determining whether or not the DNA of said strain has an NciI-MspI restriction site comprising the codon corresponding to codon 463 of the *M. tuberculosis* katG gene consensus sequence depicted in FIG. 7 (SEQ ID NO:20), wherein the absence of said restriction site is indicative of an INH resistant strain.

2. The method of claim 1 which comprises the step of:

(a) amplifying a portion of the katG gene of an *M. tuberculosis* isolate to yield a detectable amount of DNA comprising the nucleotide position occupied by base 1457 of the *M. tuberculosis* katG gene consensus sequence depicted in FIG. 7 (SEQ ID NO:20);

(b) cleaving the amplified DAN with a restriction endonuclease which cleaves at an NciI-MspI restriction site to yield at least one DNA fragment; and (c) employing the technique of gel electrophoresis to determine whether the number and location of the DNA fragments is indicative of the absence of an NciI-MspI restriction site comprising codon 463 of said katG gene, wherein said absence is indicative of an INH resistant strain of *M. tuberculosis* in said isolate.

3. The method of claim 2 wherein the amplified DNA comprises 4 NciI-MspI restriction sites prior to cleavage.

4. The method of claim 1 wherein polymerase chain reaction (PCR) is employed to amplify DNA from the katG gene of the isolate of *M. tuberculosis* to be assayed.

5. The method of claim 4 wherein said DNA is amplified employing two oligonucleotide primers of the sequence (5' CACCCCACGAAATGGGACAACAGTTTCCT 3') (SEQ ID NO:5) and (5' GGGTCTGACAAATCGCGC-CGGGCAAACACC 3') (SEQ ID NO:6), or subunits thereof, in the PCR to yield a 1435 base pair subunit of the katG gene.

6. A method for determining the susceptibility of a strain of *M. tuberculosis* to isoniazid comprising determining whether or not the DNA comprising the katG gene of said strain has a mutated base, which mutated base is a T at the nucleotide position occupied by base 1457 in codon 463 of the *M. tuberculosis* katG gene consensus sequence, which codon 463 is represented by bases 1456 through 1458 depicted in FIG. 7 (SEQ ID NO:20), or a C at the nucleotide position occupied by base 1013 in codon 315 of the *M. tuberculosis* katG gene consensus sequence, which codon 315 is represented by bases 1012 through 1014 depicted in FIG. 7 (SEQ ID NO:20), and wherein said mutated base is indicative of an INH resistant strain.

7. The method of claim 6 comprising the steps of:

(a) selecting a restriction endonuclease which cleaves at either a wild-type restriction site or a corresponding mutant restriction site present on DNA comprising an *M. tuberculosis* katG gene, but not at both of said wild-type and corresponding mutant sites, wherein (1) said wild-type restriction site comprises (i) a G at the nucleotide position occupied by base 1457 in codon 463 of the *M. tuberculosis* katG gene consensus sequence, which codon 463 is represented by bases 1456 through 1458 depicted in FIG. 7 (SEQ ID NO:20), or (ii) a G at the nucleotide position occupied by base 1013 in codon 315 of the *M. tuberculosis* katG gene consensus sequence, which codon 315 is represented by bases 1012 through 1014 depicted in FIG. 7 (SEQ ID NO:20), and wherein (2) said corresponding mutant restriction site comprises (i) a T at the nucleotide position occupied by base 1457 in codon 463 of the *M. tuberculosis* katG gene consensus sequence, which codon 463 is represented by bases 1456 through 1458 depicted in FIG. 7 (SEQ ID NO:20), or (ii) a C at the nucleotide position occupied by base 1013 in codon 315 of the *M. tuberculosis* katG gene consensus sequence, which codon 315 is represented by bases 1012 through 1014 depicted in FIG. 7 (SEQ 1D NO:20);

(b) amplifying a portion of the katG gene of an *M. tuberculosis* isolate to yield a detectable amount of DNA comprising the nucleotide positions occupied by said wild-type restriction site or corresponding mutant restriction site, which site is cleaved by the selected restriction endonuclease;

(c) cleaving the amplified DNA with the selected restriction endonuclease to yield at least one DNA fragment; and (d) employing the technique of gel electrophoresis to determine whether the number and location of the DNA fragments is indicative of the presence of said mutated base at the positions occupied by base 1457 or base 1013 of the *M. tuberculosis* katG gene consensus sequence depicted in FIG. 7 (SEQ ID NO:20), which presence of a mutated base is indicative of an isoniazid resistant strain of *M. tuberculosis* in said isolate.

8. The method of claim 7, wherein the amplified DNA of the *M. tuberculosis* isolate in step (b) further comprises at least one additional restriction site, which restriction site is cleaved by the selected restriction endonuclease.

9. The method of claim 7, further comprising (e) amplifying a portion of the wild-type *M. tuberculosis* katG gene equivalent to the portion amplified in step (b), which wild-type gene has the consensus sequence depicted in FIG. 7 (SEQ ID NO:20), to yield a detectable amount of wild-type DNA;

(f) cleaving the amplified wild-type DNA with the selected restriction enzyme to yield at least one wild-type DNA fragment;

(g) employing the technique of gel electrophoresis to separate the wild-type DNA fragments;

(h) using restriction fragment length polymorphism (RFLP) analysis to compare the number and location of the DNA fragments of the *M. tuberculosis* isolate in step (d) to the number and location of the wild-type DNA fragments in step (g) to determine whether the amplified portion of the katG gene of the *M. tuberculosis* isolate comprises a different number of restriction sites cleaved by said selected restriction enzyme, said difference being indicative of an isoniazid resistant strain of *M. tuberculosis* in said isolate.

10. A method for determining the susceptibility of a strain of *M. tuberculosis* to isoniazid comprising determining whether or not DNA comprising the katG gene of said strain has a restriction site selected from the group consisting of:

(a) an NciI-MspI restriction site comprising the nucleotide position occupied by base 1457 in codon 463 of the *M. tuberculosis* katG gene consensus sequence, which codon 463 is represented by bases 1456 through 1458 depicted in FIG. 7 (SEQ ID NO:20);

(b) an MspI restriction site comprising the nucleotide position occupied by base 1013 in codon 315 of the *M. tuberculosis* katG gene consensus sequence, which codon 315 is represented by bases 1012 through 1014 depicted in FIG. 7 (SEQ ID NO:20); and (c) a BstNI restriction site comprising the nucleotide position occupied by base 1457 in codon 463 of the *M. tuberculosis* katG gene consensus sequence, which codon 463 is represented by bases 1456 through 1458 depicted in FIG. 7 (SEQ ID NO:20);

wherein each of the absence of an NciI-MspI restriction site associated with codon 463, the presence of an MspI restriction site associated with codon 315, and the presence of a BstNI restriction site associated with codon 463 is indicative of an isoniazid resistant strain of *M. tuberculosis*.

11. A method for determining the susceptibility of a strain of *M. tuberculosis* to isoniazid comprising the steps of:

(a) amplifying a portion of the katG gene of an *M. tuberculosis* isolate to yield a detectable amount of DNA comprising at least one MspI restriction site, and nucleotide positions occupied by bases 1013 and 1457 of the *M. tuberculosis* katG gene consensus sequence depicted in FIG. 7 (SEQ ID NO:20);

(b) cleaving the amplified DNA with a restriction endonuclease at said restriction site to yield DNA fragments; and (c) employing the technique of gel electrophoresis to determine whether the number and location of the DNA fragments is indicative of (1) the presence on said portion of the katG gene of an MspI restriction site associated with codon 315, which associated MspI restriction site comprises the nucleotide position occupied by base 1013 of the *M. tuberculosis* katG gene consensus sequence depicted in FIG. 7 (SEQ ID NO:20), or (2) the absence on said portion of the katG gene of an MspI restriction site associated with codon 463, which associated MspI restriction site comprises base 1457 of the *M. tuberculosis* katG gene consensus sequence depicted in FIG. 7 (SEQ ID NO:20), wherein each of said presence of an MspI restriction site associated with codon 315 and said absence of an MspI restriction site associated with codon 463 is indicative of an isoniazid resistant strain of *M. tuberculosis* in said isolate.

12. The method of claim 11, wherein the restriction endonuclease used to cleave the amplified DNA is MspI.

13. The method of claim 11 wherein the amplified DNA comprises nucleotide bases 904 through 1523 depicted in FIG. 7 (SEQ ID NO:20).

14. The method of claim 11 wherein polymerase chain reaction (PCR) is employed to amplify said portion of the katG gene of said isolate.

15. The method of claim 14 wherein the PCR employs the oligonucleotide primer pair of AGCTCGTATGGCACCG-GAAC (SEQ ID NO:16) and TTGACCTCCCAC-CCGACTTG (SEQ ID NO:17), or subunits thereof which hybridize to the DNA of SEQ ID NO:20.

16. The method of claim 14 wherein the PCR employs the oligonucleotides AGCTCGTATGGCACCGGAAC (SEQ ID NO: 16), TTGACCTCCCACCCGACTTG (SEQ ID NO: 17), or subunits thereof which subunits are effective for the amplification of a region of DNA incorporating codon 463 of the *M. tuberculosis* katG gene (SEQ ID NO:20).

17. An oligonucleotide selected from the group consisting of SEQ D NO:16, SEQ ID NO:17, SEQ D NO:18, SEQ ID NO:19, and subunits thereof of at least 7 bases which subunits are effective for the amplification of a region of DNA incorporating codon 463 of the *M. tuberculosis katG gene (SEQ ID NO:20).

18. The oligonucleotide of claim 17 selected from the group consisting of SEQ ID NO:16, SEQ ID NO:17, SEQ ID NO:18 and SEQ ID NO:19.

19. An isolated DNA molecule consisting of an *M. tuberculosis* katG gene, or fragment thereof of at least 7 bases, wherein said gene or fragment thereof comprises SEQ ID NO:13 OR SEQ ID NO:15.

20. A method for determining the susceptibility of a strain of *M. tuberculosis* to isoniazid comprising determining whether or not the DNA of said strain has an MspI restriction site comprising the codon corresponding to codon 315 of the *M. tuberculosis* katG gene consensus sequence depicted in FIG. 7 (SEQ ID NO:20), wherein the presence of said restriction site is indicative of an INH resistant strain.

\* \* \* \* \*

UNITED STATES PATENT AND TRADEMARK OFFICE
CERTIFICATE OF CORRECTION

PATENT NO.    : 5,658,733
DATED         : August 19, 1997
INVENTOR(S)   : Franklin R. Cockerill, III, et al.

It is certified that error appears in the above-identified patent and that said Letters Patent is hereby corrected as shown below:

Column 1,
Line 29, delete "made" and insert -- mode --;

Column 4,
Line 17, delete "463 is determination" and insert -- 463 is present, wherein a determination --;

Column 9,
Line 56, delete "serine → leucine" and insert -- serine → threonine --;

Column 13,
Line 53, delete "that is" and insert -- that it is --;

Column 14,
Line 66, delete "restriction sites" and insert -- restriction site --;

Column 15,
Line 8, delete "katG904katG1523" and insert -- katG904/katG1523 --;
Line 11, delete "katG633katG983" and insert -- katG633/katG983 --;
Line 44, delete "10 units/m/" and insert -- 10 units/ml --;

Column 16,
Line 20, delete "codon 315" and insert -- codon 463 --; and

Column 41,
Line 25, delete "amplified DAN" and insert -- amplified DNA --.

Signed and Sealed this

Ninth Day of October, 2001

Attest:

NICHOLAS P. GODICI
*Attesting Officer*           *Acting Director of the United States Patent and Trademark Office*

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
( A ) LENGTH: 2235 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:1:

| | | | | | | |
|---|---|---|---|---|---|---|
| AGGAATGCTG | TGCCCGAGCA | ACACCCACCC | ATTACAGAAA | CCACCACCGG | AGCCGCTAGC | 60 |
| AACGGCTGTC | CCGTCGTGGG | TCATATGAAA | TACCCCGTCG | AGGGCGGCGG | AAACCAGGAC | 120 |
| TGGTGGCCCA | ACCGGCTCAA | TCTGAAGGTA | CTGCACCAAA | ACCCGGCCGT | CGCTGACCCG | 180 |
| ATGGGTGCGG | CGTTCGACTA | TGCCGCGGAG | GTCGCGACCA | TCGACGTTGA | CGCCCTGACG | 240 |
| CGGGACATCG | AGGAAGTGAT | GACCACCTCG | CAGCCGTGGT | GGCCCGCCGA | CTACGGCCAC | 300 |
| TACGGGCCGC | TGTTTATCCG | GATGGCGTGG | CACGCTGCCG | GCACCTACCG | CATCCACGAC | 360 |
| GGCCGCGGCG | GCGCCGGGGG | CGGCATGCAG | CGGTTCGCGC | CGCTTAACAG | CTGGCCCGAC | 420 |
| AACGCCAGCT | TGGACAAGGC | GCGCCGGCTG | CTGTGGCCGG | TCAAGAAGAA | GTACGGCAAG | 480 |
| AAGCTCTCAT | GGGCGGACCT | GATTGTTTTC | GCCGGCAACT | GCGCGCTGGA | ATCGATGGGC | 540 |
| TTCAAGACGT | TCGGGTTCGG | CTTCGGCCGG | GTCGACCAGT | GGGAGCCCGA | TGAGGTCTAT | 600 |
| TGGGGCAAGG | AAGCCACCTG | GCTCGGCGAT | GAGCGTTACA | GCGGTAAGCG | GGATCTGGAG | 660 |
| AACCCGCTGG | CCGCGGTGCA | GATGGGGCTG | ATCTACGTGA | ACCCGGAGGG | GCCGAACGGC | 720 |
| AACCCGGACC | CCATGGCCGC | GGCGGTCGAC | ATTCGCGAGA | CGTTTCGGCG | CATGGCCATG | 780 |
| AACGACGTCG | AAACAGCGGC | GCTGATCGTC | GGCGGTCACA | CTTTCGGTAA | GACCCATGGC | 840 |
| GCCGGCCCGG | CCGATCTGGT | CGGCCCCGAA | CCCGAGGCTG | CTCCGCTGGA | GCAGATGGGC | 900 |
| TTGGGCTGGA | AGAGCTCGTA | TGGCACCGGA | ACCGGTAAGG | ACGCGATCAC | CAGCGGCATC | 960 |
| GAGGTCGTAT | GGACGAACAC | CCCGACGAAA | TGGACAACA | GTTTCCTCGA | GATCCTGTAC | 1020 |
| GGCTACGAGT | GGGAGCTGAC | GAAGAGCCCT | GCTGGCGCTT | GGCAATACAC | CGCCAAGGAC | 1080 |
| GGCGCCGGTG | CCGGCACCAT | CCCGGACCCG | TTCGGCGGGC | CAGGGCGCTC | CCCGACGATG | 1140 |
| CTGGCCACTG | ACCTCTCGCT | GCGGGTGGAT | CCGATCTATG | AGCGGATCAC | GCGTCGCTGG | 1200 |
| CTGGAACACC | CCGAGGAATT | GGCCGACGAG | TTCGCCAAGG | CCTGGTACAA | GCTGATCCAC | 1260 |
| CGAGACATGG | GTCCCGTTGC | GAGATACCTT | GGGCCGCTGG | TCCCAAGCA | GACCCTGCTG | 1320 |
| TGGCAGGATC | CGGTCCCTGC | GGTCAGCCAC | GACCTCGTCG | GCGAAGCCGA | GATTGCCAGC | 1380 |
| CTTAAGAGCC | AGATCCGGGC | ATCGGGATTG | ACTGTCTCAC | AGCTAGTTTC | GACCGCATGG | 1440 |

| | | | | | |
|---|---|---|---|---|---|
| GCGGCGGCGT | CGTCGTTCCG | TGGTAGCGAC | AAGCGCGGCG | GCGCCAACGG | TGGTCGCATC | 1500 |
| CGCCTGCAGC | CACAAGTCGG | GTGGGAGGTC | AACGACCCCG | ACGGGATCT | GCGCAAGGTC | 1560 |
| ATTCGCACCC | TGGAAGAGAT | CCAGGAGTCA | TTCAACTCCG | CGGCGCCGGG | GAACATCAAA | 1620 |
| GTGTCCTTCG | CCGACCTCGT | CGTGCTCGGT | GGCTGTGCCG | CCATAGAGAA | AGCAGCAAAG | 1680 |
| GCGGCTGGCC | ACAACATCAC | GGTGCCCTTC | ACCCCGGGCC | GCACGGATGC | GTCGCAGGAA | 1740 |
| CAAACCGACG | TGGAATCCTT | TGCCGTGCTG | GAGCCCAAGG | CAGATGGCTT | CCGAAACTAC | 1800 |
| CTCGGAAAGG | GCAACCCGTT | GCCGGCCGAG | TACATGCTGC | TCGACAAGGC | GAACCTGCTT | 1860 |
| ACGCTCAGTG | CCCCTGAGAT | GACGGTGCTG | GTAGGTGGCC | TGCGCGTCCT | CGGGCAAACT | 1920 |
| ACAAGCGCTT | ACCGCTGGGC | GTGTTCACCG | AGGCCTCCGA | GTCACTGACC | AACGACTTCT | 1980 |
| TCGTGAACCT | GCTCGACATG | GGTATCACCT | GGGAGCCCTC | GCCAGCAGAT | GACGGGACCT | 2040 |
| ACCAGGGCAA | GGATGGCAGT | GGCAAGGTGA | AGTGGACCGG | CAGCCGCGTG | GACCTGGTCT | 2100 |
| TCGGGTCCAA | CTCGGAGTTG | CGGGCGCTTG | TCGAGGTCTA | TGGCGCCGAT | GACGCGCAGC | 2160 |
| CGAAGTTCGT | GCAGGACTTC | GTCGCTGCCT | GGGACAAGGT | GATGAACCTC | GACAGGTTCG | 2220 |
| ACGTGCGCTG | ATTCG | | | | | 2235 |

( 2 ) INFORMATION FOR SEQ ID NO:2:

( i ) SEQUENCE CHARACTERISTICS:
        ( A ) LENGTH: 2221 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

| | | | | | |
|---|---|---|---|---|---|
| AGGAATGCTG | TGCCCGAGCA | ACACCCACCC | ATTACAGAAA | CCACCACCGG | AGCCGCTAGC | 60 |
| AACGGCTGTC | CCGTCGTGGG | TCATATGAAA | TACCCCGTCG | AGGGCGGCGG | AAACCAGGAC | 120 |
| TGGTGGCCCA | ACCGGCTCAA | TCTGAAGGTA | CTGCACCAAA | ACCCGGCCGT | CGCTGACCCG | 180 |
| ATGGGTGCGG | CGTTCGACTA | TGCCGCGGAG | GTCGCGACCA | GTCGACTTGA | CGCCCTGACG | 240 |
| CGGGACATCG | AGGAAGTGAT | GACCACCTCG | CAGCCGTGGT | GGCCCGCCGA | CTACGGCCAC | 300 |
| TACGGGCCGC | TGTTTATCCG | GATGGCGTGG | CACGCTGCCG | GCACCTACCG | CATCCACGAC | 360 |
| GGCCGCGGCG | GCGCCGGGGG | CGGCATGCAG | CGGTTCGCGC | CGCTTAACAG | CTGGCCCGAC | 420 |
| AACGCCAGCT | TGGACAAGGC | GCGCCGGCTG | CTGTGGCCGG | TCAAGAAGAA | GTACGGCAAG | 480 |
| AAGCTCTCAT | GGGCGGACCT | GATTGTTTTC | GCCGGCAACC | GCTGCGCTCG | GAATCGATGG | 540 |
| GCTTCAAGAC | GTTCGGGTTC | GGCTTCGGGC | GTCGACCAGT | GGGAGACCGA | TGAGGTCTAT | 600 |
| TGGGCAAGG | AAGCCACCTG | GCTCGGCGAT | GACGGTTACA | GCGTAAGCGA | TCTGGAGAAC | 660 |
| CCGCTGGCCG | CGGTGCAGAT | GGGGCTGATC | TACGTGAACC | GGAGGCGCC | GAACGGCAAC | 720 |
| CCGGACCCCA | TGGCCGCGGC | GGTCGACATT | CGCGAGACGT | TTCGGCGCAT | GGCCATGAAC | 780 |
| GACGTCGAAA | CAGCGGCGCT | GATCGTCGGC | GGTCACACTT | TCGGTAAGAC | CCATGGCGCC | 840 |
| GGCCCGGCCG | ATCTGGTCGG | CCCCGAACCC | GAGGCTGCTC | CGCTGGAGCA | GATGGGCTTG | 900 |
| GGCTGGAAGA | GCTCGTATGG | CACCGGAACC | GGTAAGGACG | CGATCACCAG | CGGCATCGAG | 960 |
| GTCGTATGGA | CGAACACCCC | GACGAAATGG | GACAACAGTT | CCTCGAGAT | CCTGTACGGC | 1020 |
| TACGAGTGGG | AGCTGACGAA | GAGCCCTGCT | GGCGCTTGGC | AATACACCGC | CAAGGACGGC | 1080 |
| GCCGGTGCCG | GCACCATCCC | GGACCCGTTC | GGCGGGCCAG | GGCGCTCCCC | GACGATGCTG | 1140 |
| GCCACTGACC | TCTCGCTGCG | GGTGGATCCG | ATCTATGAGC | GGATCACGCG | TCGCTGGCTG | 1200 |

| | | | | | |
|---|---|---|---|---|---|
| GAACACCCCG | AGGAATTGGC | CGACGAGTTC | CGCAAGGCCT | GGTACAAGCT | GATCCACCGA 1260 |
| GACATGGGTC | CCGTTGCGAG | ATACCTTGGG | CCGCTGGTCC | CCAAGCAGAC | CCTGCTGTGG 1320 |
| CAGGATCCGG | TCCCTGCGGT | CAGCACGACC | TCGTCGGCGA | AGCAGATTGC | CAGCCTTAAG 1380 |
| AGCCAGATCC | GGGCATCGGG | ATTGACTGTC | TCACAGCTAG | TTTCGACCGC | ATGGGCGGCG 1440 |
| GCGTCGTCGT | TCCGTGGTAG | CGACAAGCGC | GGCGGCGCCA | ACGGTGGTCG | CATCCGCCTG 1500 |
| CAGCCACAAG | TCGGGTGGGA | GGTCAACGAC | CCCGACGGAT | CTGCGCAAGG | TCATTCGCAC 1560 |
| CCTGAAGAGA | TCCAGGAGTC | ATTCACTCGG | CGCGGGAACA | TCAAAGTGTC | CTTCGCCGAC 1620 |
| CTCGTCGTGC | TCGGTGGCTG | TGCGCCACTA | GAGAAAGCAG | CAAAGGCGGC | TGGCCACAAC 1680 |
| ATCACGGTGC | CCTTCACCCC | GGGCCCGCAC | GATGCGTCGC | AGGAACAAAC | CGACGTGGAA 1740 |
| TCCTTTGCCG | TGCTGGAGCC | CAAGGCAGAT | GGCTTCCGAA | ACTACCTCGG | AAAGGGCAAC 1800 |
| CGTTGCCGGC | CGAGTACATC | GCTGCTCGAC | AAGGCGAACC | TGCTTACGCT | CAGTGCCCCT 1860 |
| GAGATGACGG | TGCTGGTAGG | TGGCCTGCGC | GTCCTCGGCG | CAAACTACAA | GCGCTTACCG 1920 |
| CTGGGCGTGT | TCACCGAGGC | CTCCGAGTCA | CTGACCAACG | ACTTCTTCGT | GAACCTGCTC 1980 |
| GACATGGGTA | TCACCTGGGA | GCCCTCGCCA | GCAGATGACG | GGACCTACCA | GGGCAAGGAT 2040 |
| GGCAGTGGCA | AGGTGAAGTG | GACCGGCAGC | CGCGTGGACC | TGGTCTTCGG | GTCCAACTCG 2100 |
| GAGTTGCGGG | CGCTTGTCGA | GGTCTATGCG | CCGATGACGC | GGCAGGCGAA | GTTCGTGACA 2160 |
| GGATTCGTCG | CTGCGTGGGA | CAAGGTGATG | AACCTCGACA | GGTTCGACGT | GCGCTGATTC 2220 |
| G | | | | | 2221 |

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

TCGGACCATA ACGGCTTCCT GTTGGACGAG                                    30

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

AATCTGCTTC GCCGACGAGG TCGTGCTGAC                                    30

( 2 ) INFORMATION FOR SEQ ID NO:5:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:5:

CACCCCGACG AAATGGGACA ACAGTTTCCT 30

( 2 ) INFORMATION FOR SEQ ID NO:6:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

GGGTCTGACA AATCGCGCCG GGCAAACACC 30

( 2 ) INFORMATION FOR SEQ ID NO:7:

( i ) SEQUENCE CHARACTERISTICS:
        ( A ) LENGTH: 740 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:7:

```
Val Pro Glu Gly His Pro Pro Ile Thr Glu Thr Thr Thr Gly Ala Ala
 1               5                  10                  15

Ser Asn Gly Cys Pro Val Val Gly His Met Lys Tyr Pro Val Glu Gly
            20                  25                  30

Gly Gly Asn Gln Asp Trp Trp Pro Asn Arg Leu Asn Leu Lys Val Leu
         35                  40                  45

His Gln Asn Pro Ala Val Ala Asp Pro Met Gly Ala Ala Phe Asp Tyr
     50                  55                  60

Ala Ala Glu Val Ala Thr Ile Asp Val Asp Ala Leu Thr Arg Asp Ile
 65                  70                  75                  80

Glu Glu Val Met Thr Thr Ser Gln Pro Trp Trp Pro Ala Asp Tyr Gly
                 85                  90                  95

His Tyr Gly Pro Leu Phe Ile Arg Met Ala Trp His Ala Ala Gly Thr
            100                 105                 110

Tyr Arg Ile His Asp Gly Arg Gly Gly Ala Gly Gly Gly Met Gln Arg
         115                 120                 125

Phe Ala Pro Leu Asn Ser Trp Pro Asp Asn Ala Ser Leu Asp Lys Ala
    130                 135                 140

Arg Arg Leu Leu Trp Pro Val Lys Lys Lys Tyr Gly Lys Lys Leu Ser
145                 150                 155                 160

Trp Ala Asp Leu Ile Val Phe Ala Gly Asn Cys Ala Leu Glu Ser Met
                165                 170                 175

Gly Phe Lys Thr Phe Gly Phe Gly Phe Gly Arg Val Asp Gln Trp Glu
            180                 185                 190

Pro Asp Glu Val Tyr Trp Gly Lys Glu Ala Thr Trp Leu Gly Asp Glu
        195                 200                 205

Arg Tyr Ser Gly Lys Arg Asp Leu Glu Asn Pro Leu Ala Ala Val Gln
    210                 215                 220

Met Gly Leu Ile Tyr Val Asn Pro Glu Gly Pro Asn Gly Asn Pro Asp
225                 230                 235                 240

Pro Met Ala Ala Ala Val Asp Ile Arg Glu Thr Phe Arg Arg Met Ala
                245                 250                 255

Met Asn Asp Val Glu Thr Ala Ala Leu Ile Val Gly Gly His Thr Phe
            260                 265                 270
```

```
Gly Lys Thr His Gly Ala Gly Pro Ala Asp Leu Val Gly Pro Glu Pro
        275                 280                 285
Glu Ala Ala Pro Leu Glu Gln Met Gly Leu Gly Trp Lys Ser Ser Tyr
    290                 295                 300
Gly Thr Gly Thr Gly Lys Asp Ala Ile Thr Ser Gly Ile Glu Val Val
305                     310                 315                 320
Trp Thr Asn Thr Pro Thr Lys Trp Asp Asn Ser Phe Leu Glu Ile Leu
                325                 330                 335
Tyr Gly Tyr Glu Trp Glu Leu Thr Lys Ser Pro Ala Gly Ala Trp Gln
            340                 345                 350
Tyr Thr Ala Lys Asp Gly Ala Gly Ala Gly Thr Ile Pro Asp Pro Phe
        355                 360                 365
Gly Gly Pro Gly Arg Ser Pro Thr Met Leu Ala Thr Asp Leu Ser Leu
370                 375                 380
Arg Val Asp Pro Ile Tyr Glu Arg Ile Thr Arg Arg Trp Leu Glu His
385                 390                 395                 400
Pro Glu Glu Leu Ala Asp Glu Phe Ala Lys Ala Trp Tyr Lys Leu Ile
                405                 410                 415
His Arg Asp Met Gly Pro Val Ala Arg Tyr Leu Gly Pro Leu Val Pro
            420                 425                 430
Lys Gln Thr Leu Leu Trp Gln Asp Pro Val Pro Ala Val Ser His Asp
        435                 440                 445
Leu Val Gly Glu Ala Glu Ile Ala Ser Leu Lys Ser Gln Ile Arg Ala
    450                 455                 460
Ser Gly Leu Thr Val Ser Gln Leu Val Ser Thr Ala Trp Ala Ala Ala
465                 470                 475                 480
Ser Ser Phe Arg Gly Ser Asp Lys Arg Gly Gly Ala Asn Gly Gly Arg
                485                 490                 495
Ile Arg Leu Gln Pro Gln Val Gly Trp Glu Val Asn Asp Pro Asp Gly
            500                 505                 510
Asp Leu Arg Lys Val Ile Arg Thr Leu Glu Glu Ile Gln Glu Ser Phe
        515                 520                 525
Asn Ser Ala Ala Pro Gly Asn Ile Lys Val Ser Phe Ala Asp Leu Val
    530                 535                 540
Val Leu Gly Gly Cys Ala Ala Ile Glu Lys Ala Ala Lys Ala Ala Gly
545                 550                 555                 560
His Asn Ile Thr Val Pro Phe Thr Pro Gly Arg Thr Asp Ala Ser Gln
                565                 570                 575
Glu Gln Thr Asp Val Glu Ser Phe Ala Val Leu Glu Pro Lys Ala Asp
            580                 585                 590
Gly Phe Arg Asn Tyr Leu Gly Lys Gly Asn Pro Leu Pro Ala Glu Tyr
        595                 600                 605
Met Leu Leu Asp Lys Ala Asn Leu Leu Thr Leu Ser Ala Pro Glu Met
    610                 615                 620
Thr Val Leu Val Gly Gly Leu Arg Val Leu Gly Ala Asn Tyr Lys Arg
625                 630                 635                 640
Leu Pro Leu Gly Val Phe Thr Glu Ala Ser Glu Ser Leu Thr Asn Asp
                645                 650                 655
Phe Phe Val Asn Leu Leu Asp Met Gly Ile Thr Trp Glu Pro Ser Pro
            660                 665                 670
Ala Asp Asp Gly Thr Tyr Gln Gly Lys Asp Gly Ser Gly Lys Val Lys
        675                 680                 685
Trp Thr Gly Ser Arg Val Asp Leu Val Phe Gly Ser Asn Ser Glu Leu
```

|   |   |   |   | 690 |   |   |   | 695 |   |   |   | 700 |   |   |
|---|---|---|---|---|---|---|---|---|---|---|---|---|---|---|

Arg Ala Leu Val Glu Val Tyr Gly Ala Asp Asp Ala Gln Pro Lys Phe
705                     710                 715                 720

Val Gln Asp Phe Val Ala Ala Trp Asp Lys Val Met Asn Leu Asp Arg
                725                 730                 735

Phe Asp Val Arg
            740

( 2 ) INFORMATION FOR SEQ ID NO:8:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:8:

GTCGAAACAG CGGCGCTGAT CGTCGGC 27

( 2 ) INFORMATION FOR SEQ ID NO:9:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:9:

GTCGAAACAG CGACGCTGAT CGTCGGC 27

( 2 ) INFORMATION FOR SEQ ID NO:10:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:10:

CTCGAGATCC TGTACGGCTA CGAGTGG 27

( 2 ) INFORMATION FOR SEQ ID NO:11:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:11:

CTCGAGATCC TGTGCGGCTA CGAGTGG 27

( 2 ) INFORMATION FOR SEQ ID NO:12:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:12:

GACGCGATCA CCAGCGGCAT CGAGGTC　　　　　　　　　　　　　　　　　　　　　　　　　27

( 2 ) INFORMATION FOR SEQ ID NO:13:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:13:

GACGCGATCA CCACCGGCAT CGAGGTC　　　　　　　　　　　　　　　　　　　　　　　　　27

( 2 ) INFORMATION FOR SEQ ID NO:14:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:14:

AAGAGCCAGA TCCGGGCATC GGGATTG　　　　　　　　　　　　　　　　　　　　　　　　　27

( 2 ) INFORMATION FOR SEQ ID NO:15:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:15:

AAGAGCCAGA TCCTGGCATC GGGATTG　　　　　　　　　　　　　　　　　　　　　　　　　27

( 2 ) INFORMATION FOR SEQ ID NO:16:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:16:

AGCTCGTATG GCACCGGAAC　　　　　　　　　　　　　　　　　　　　　　　　　　　　　20

( 2 ) INFORMATION FOR SEQ ID NO:17:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:17:

TTGACCTCCC ACCCGACTTG　　　　　　　　　　　　　　　　　　　　　　　　　　　　　20

( 2 ) INFORMATION FOR SEQ ID NO:18:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:18:

```
CGGTAAGCGG GATCTGGAGA                                                         20
```

( 2 ) INFORMATION FOR SEQ ID NO:19:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:19:

```
CATTTCGTCG GGGTGTTCGT                                                         20
```

( 2 ) INFORMATION FOR SEQ ID NO:20:

( i ) SEQUENCE CHARACTERISTICS:
        ( A ) LENGTH: 2331 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: CDS
        ( B ) LOCATION: 70..2289

( x i ) SEQUENCE DESCRIPTION: SEQ ID NO:20:

```
CGATATCCGA CACTTCGCGA TCACATCCGT GATCACAGCC CGATAACACC AACTCCTGGA             60

AGGAATGCT GTG CCC GAG CAA CAC CCA CCC ATT ACA GAA ACC ACC ACC               108
          Val Pro Glu Gln His Pro Pro Ile Thr Glu Thr Thr Thr
            1               5                  10

GGA GCC GCT AGC AAC GGC TGT CCC GTC GTG GGT CAT ATG AAA TAC CCC             156
Gly Ala Ala Ser Asn Gly Cys Pro Val Val Gly His Met Lys Tyr Pro
    15                  20                  25

GTC GAG GGC GGC GGA AAC CAG GAC TGG TGG CCC AAC CGG CTC AAT CTG             204
Val Glu Gly Gly Gly Asn Gln Asp Trp Trp Pro Asn Arg Leu Asn Leu
 30                  35                  40                  45

AAG GTA CTG CAC CAA AAC CCG GCC GTC GCT GAC CCG ATG GGT GCG GCG             252
Lys Val Leu His Gln Asn Pro Ala Val Ala Asp Pro Met Gly Ala Ala
                 50                  55                  60

TTC GAC TAT GCC GCG GAG GTC GCG ACC ATC GAC GTT GAC GCC CTG ACG             300
Phe Asp Tyr Ala Ala Glu Val Ala Thr Ile Asp Val Asp Ala Leu Thr
             65                  70                  75

CGG GAC ATC GAG GAA GTG ATG ACC ACC TCG CAG CCG TGG TGG CCC GCC             348
Arg Asp Ile Glu Glu Val Met Thr Thr Ser Gln Pro Trp Trp Pro Ala
         80                  85                  90

GAC TAC GGC CAC TAC GGG CCG CTG TTT ATC CGG ATG GCG TGG CAC GCT             396
Asp Tyr Gly His Tyr Gly Pro Leu Phe Ile Arg Met Ala Trp His Ala
     95                 100                 105

GCC GGC ACC TAC CGC ATC CAC GAC GGC CGC GGC GGC GCC GGG GGC GGC             444
Ala Gly Thr Tyr Arg Ile His Asp Gly Arg Gly Gly Ala Gly Gly Gly
```

-continued

| | | | | | | | | | | | | | | | |
|---|---|---|---|---|---|---|---|---|---|---|---|---|---|---|---|
| 110 | | | | | 115 | | | | | 120 | | | | 125 | |

```
ATG CAG CGG TTC GCG CCG CTT AAC AGC TGG CCC GAC AAC GCC AGC TTG        492
Met Gln Arg Phe Ala Pro Leu Asn Ser Trp Pro Asp Asn Ala Ser Leu
            130                     135                 140

GAC AAG GCG CGC CGG CTG CTG TGG CCG GTC AAG AAG AAG TAC GGC AAG        540
Asp Lys Ala Arg Arg Leu Leu Trp Pro Val Lys Lys Lys Tyr Gly Lys
                145                 150                 155

AAG CTC TCA TGG GCG GAC CTG ATT GTT TTC GCC GGC AAC TGC GCG CTG        588
Lys Leu Ser Trp Ala Asp Leu Ile Val Phe Ala Gly Asn Cys Ala Leu
            160                 165                 170

GAA TCG ATG GGC TTC AAG ACG TTC GGG TTC GGC TTC GGC CGG GTC GAC        636
Glu Ser Met Gly Phe Lys Thr Phe Gly Phe Gly Phe Gly Arg Val Asp
        175                 180                 185

CAG TGG GAG CCC GAT GAG GTC TAT TGG GGC AAG GAA GCC ACC TGG CTC        684
Gln Trp Glu Pro Asp Glu Val Tyr Trp Gly Lys Glu Ala Thr Trp Leu
190                 195                 200                 205

GGC GAT GAG CGT TAC AGC GGT AAG CGG GAT CTG GAG AAC CCG CTG GCC        732
Gly Asp Glu Arg Tyr Ser Gly Lys Arg Asp Leu Glu Asn Pro Leu Ala
                    210                 215                 220

GCG GTG CAG ATG GGG CTG ATC TAC GTG AAC CCG GAG GGG CCG AAC GGC        780
Ala Val Gln Met Gly Leu Ile Tyr Val Asn Pro Glu Gly Pro Asn Gly
                225                 230                 235

AAC CCG GAC CCC ATG GCC GCG GCG GTC GAC ATT CGC GAG ACG TTT CGG        828
Asn Pro Asp Pro Met Ala Ala Ala Val Asp Ile Arg Glu Thr Phe Arg
            240                 245                 250

CGC ATG GCC ATG AAC GAC GTC GAA ACA GCG GCG CTG ATC GTC GGC GGT        876
Arg Met Ala Met Asn Asp Val Glu Thr Ala Ala Leu Ile Val Gly Gly
        255                 260                 265

CAC ACT TTC GGT AAG ACC CAT GGC GCC GGC CCG GCC GAT CTG GTC GGC        924
His Thr Phe Gly Lys Thr His Gly Ala Gly Pro Ala Asp Leu Val Gly
270                 275                 280                 285

CCC GAA CCC GAG GCT GCT CCG CTG GAG CAG ATG GGC TTG GGC TGG AAG        972
Pro Glu Pro Glu Ala Ala Pro Leu Glu Gln Met Gly Leu Gly Trp Lys
                    290                 295                 300

AGC TCG TAT GGC ACC GGA ACC GGT AAG GAC GCG ATC ACC AGC GGC ATC       1020
Ser Ser Tyr Gly Thr Gly Thr Gly Lys Asp Ala Ile Thr Ser Gly Ile
                305                 310                 315

GAG GTC GTA TGG ACG AAC ACC CCG ACG AAA TGG GAC AAC AGT TTC CTC       1068
Glu Val Val Trp Thr Asn Thr Pro Thr Lys Trp Asp Asn Ser Phe Leu
            320                 325                 330

GAG ATC CTG TAC GGC TAC GAG TGG GAG CTG ACG AAG AGC CCT GCT GGC       1116
Glu Ile Leu Tyr Gly Tyr Glu Trp Glu Leu Thr Lys Ser Pro Ala Gly
        335                 340                 345

GCT TGG CAA TAC ACC GCC AAG GAC GGC GCC GGT GCC GGC ACC ATC CCG       1164
Ala Trp Gln Tyr Thr Ala Lys Asp Gly Ala Gly Ala Gly Thr Ile Pro
350                 355                 360                 365

GAC CCG TTC GGC GGG CCA GGG CGC TCC CCG ACG ATG CTG GCC ACT GAC       1212
Asp Pro Phe Gly Gly Pro Gly Arg Ser Pro Thr Met Leu Ala Thr Asp
                    370                 375                 380

CTC TCG CTG CGG GTG GAT CCG ATC TAT GAG CGG ATC ACG CGT CGC TGG       1260
Leu Ser Leu Arg Val Asp Pro Ile Tyr Glu Arg Ile Thr Arg Arg Trp
                385                 390                 395

CTG GAA CAC CCC GAG GAA TTG GCC GAC GAG TTC GCC AAG GCC TGG TAC       1308
Leu Glu His Pro Glu Glu Leu Ala Asp Glu Phe Ala Lys Ala Trp Tyr
            400                 405                 410

AAG CTG ATC CAC CGA GAC ATG GGT CCC GTT GCG AGA TAC CTT GGG CCG       1356
Lys Leu Ile His Arg Asp Met Gly Pro Val Ala Arg Tyr Leu Gly Pro
        415                 420                 425

CTG GTC CCC AAG CAG ACC CTG CTG TGG CAG GAT CCG GTC CCT GCG GTC       1404
Leu Val Pro Lys Gln Thr Leu Leu Trp Gln Asp Pro Val Pro Ala Val
```

```
          430                    435                         440                        445
 AGC CAC GAC CTC GTC GGC GAA GCC GAG ATT GCC AGC CTT AAG AGC CAG                1452
 Ser His Asp Leu Val Gly Glu Ala Glu Ile Ala Ser Leu Lys Ser Gln
                     450                 455                 460

ATC CGG GCA TCG GGA TTG ACT GTC TCA CAG CTA GTT TCG ACC GCA TGG                1500
 Ile Arg Ala Ser Gly Leu Thr Val Ser Gln Leu Val Ser Thr Ala Trp
                 465                 470                 475

GCG GCG GCG TCG TCG TTC CGT GGT AGC GAC AAG CGC GGC GGC GCC AAC                1548
 Ala Ala Ala Ser Ser Phe Arg Gly Ser Asp Lys Arg Gly Gly Ala Asn
                 480                 485                 490

GGT GGT CGC ATC CGC CTG CAG CCA CAA GTC GGG TGG GAG GTC AAC GAC                1596
 Gly Gly Arg Ile Arg Leu Gln Pro Gln Val Gly Trp Glu Val Asn Asp
         495                 500                 505

CCC GAC GGG GAT CTG CGC AAG GTC ATT CGC ACC CTG GAA GAG ATC CAG                1644
 Pro Asp Gly Asp Leu Arg Lys Val Ile Arg Thr Leu Glu Glu Ile Gln
 510                 515                 520                 525

GAG TCA TTC AAC TCC GCG GCG CCG GGG AAC ATC AAA GTG TCC TTC GCC                1692
 Glu Ser Phe Asn Ser Ala Ala Pro Gly Asn Ile Lys Val Ser Phe Ala
                 530                 535                 540

GAC CTC GTC GTG CTC GGT GGC TGT GCC GCC ATA GAG AAA GCA GCA AAG                1740
 Asp Leu Val Val Leu Gly Gly Cys Ala Ala Ile Glu Lys Ala Ala Lys
             545                 550                 555

GCG GCT GGC CAC AAC ATC ACG GTG CCC TTC ACC CCG GGC CGC ACG GAT                1788
 Ala Ala Gly His Asn Ile Thr Val Pro Phe Thr Pro Gly Arg Thr Asp
                 560                 565                 570

GCG TCG CAG GAA CAA ACC GAC GTG GAA TCC TTT GCC GTG CTG GAG CCC                1836
 Ala Ser Gln Glu Gln Thr Asp Val Glu Ser Phe Ala Val Leu Glu Pro
     575                 580                 585

AAG GCA GAT GGC TTC CGA AAC TAC CTC GGA AAG GGC AAC CCG TTG CCG                1884
 Lys Ala Asp Gly Phe Arg Asn Tyr Leu Gly Lys Gly Asn Pro Leu Pro
 590                 595                 600                 605

GCC GAG TAC ATG CTG CTC GAC AAG GCG AAC CTG CTT ACG CTC AGT GCC                1932
 Ala Glu Tyr Met Leu Leu Asp Lys Ala Asn Leu Leu Thr Leu Ser Ala
                 610                 615                 620

CCT GAG ATG ACG GTG CTG GTA GGT GGC CTG CGC GTC CTC GGC GCA AAC                1980
 Pro Glu Met Thr Val Leu Val Gly Gly Leu Arg Val Leu Gly Ala Asn
                 625                 630                 635

TAC AAG CGC TTA CCG CTG GGC GTG TTC ACC GAG GCC TCC GAG TCA CTG                2028
 Tyr Lys Arg Leu Pro Leu Gly Val Phe Thr Glu Ala Ser Glu Ser Leu
             640                 645                 650

ACC AAC GAC TTC TTC GTG AAC CTG CTC GAC ATG GGT ATC ACC TGG GAG                2076
 Thr Asn Asp Phe Phe Val Asn Leu Leu Asp Met Gly Ile Thr Trp Glu
         655                 660                 665

CCC TCG CCA GCA GAT GAC GGG ACC TAC CAG GGC AAG GAT GGC AGT GGC                2124
 Pro Ser Pro Ala Asp Asp Gly Thr Tyr Gln Gly Lys Asp Gly Ser Gly
 670                 675                 680                 685

AAG GTG AAG TGG ACC GGC AGC CGC GTG GAC CTG GTC TTC GGG TCC AAC                2172
 Lys Val Lys Trp Thr Gly Ser Arg Val Asp Leu Val Phe Gly Ser Asn
                 690                 695                 700

TCG GAG TTG CGG GCG CTT GTC GAG GTC TAT GGC GCC GAT GAC GCG CAG                2220
 Ser Glu Leu Arg Ala Leu Val Glu Val Tyr Gly Ala Asp Asp Ala Gln
             705                 710                 715

CCG AAG TTC GTG CAG GAC TTC GTC GCT GCC TGG GAC AAG GTG ATG AAC                2268
 Pro Lys Phe Val Gln Asp Phe Val Ala Ala Trp Asp Lys Val Met Asn
     720                 725                 730

CTC GAC AGG TTC GAC GTG CGC TGATTCGGGT TGATCGGCCC TGCCCGCCGA                   2319
 Leu Asp Arg Phe Asp Val Arg
             735                 740

TCAACCACAA CC                                                                   2331
```

( 2 ) INFORMATION FOR SEQ ID NO:21:

( i ) SEQUENCE CHARACTERISTICS:
        ( A ) LENGTH: 740 amino acids
        ( B ) TYPE: amino acid
        ( D ) TOPOLOGY: linear ( i i ) MOLECULE TYPE: protein ( x i ) SEQUENCE DESCRIPTION: SEQ ID NO:21:

```
Val Pro Glu Gln His Pro Pro Ile Thr Glu Thr Thr Thr Gly Ala Ala
 1               5                  10                  15

Ser Asn Gly Cys Pro Val Val Gly His Met Lys Tyr Pro Val Glu Gly
             20                  25                  30

Gly Gly Asn Gln Asp Trp Trp Pro Asn Arg Leu Asn Leu Lys Val Leu
         35                  40                  45

His Gln Asn Pro Ala Val Ala Asp Pro Met Gly Ala Ala Phe Asp Tyr
     50                  55                  60

Ala Ala Glu Val Ala Thr Ile Asp Val Asp Ala Leu Thr Arg Asp Ile
65                  70                  75                  80

Glu Glu Val Met Thr Thr Ser Gln Pro Trp Trp Pro Ala Asp Tyr Gly
                 85                  90                  95

His Tyr Gly Pro Leu Phe Ile Arg Met Ala Trp His Ala Ala Gly Thr
            100                 105                 110

Tyr Arg Ile His Asp Gly Arg Gly Gly Ala Gly Gly Gly Met Gln Arg
        115                 120                 125

Phe Ala Pro Leu Asn Ser Trp Pro Asp Asn Ala Ser Leu Asp Lys Ala
130                 135                 140

Arg Arg Leu Leu Trp Pro Val Lys Lys Lys Tyr Gly Lys Lys Leu Ser
145                 150                 155                 160

Trp Ala Asp Leu Ile Val Phe Ala Gly Asn Cys Ala Leu Glu Ser Met
                165                 170                 175

Gly Phe Lys Thr Phe Gly Phe Gly Phe Gly Arg Val Asp Gln Trp Glu
            180                 185                 190

Pro Asp Glu Val Tyr Trp Gly Lys Glu Ala Thr Trp Leu Gly Asp Glu
        195                 200                 205

Arg Tyr Ser Gly Lys Arg Asp Leu Glu Asn Pro Leu Ala Ala Val Gln
    210                 215                 220

Met Gly Leu Ile Tyr Val Asn Pro Glu Gly Pro Asn Gly Asn Pro Asp
225                 230                 235                 240

Pro Met Ala Ala Ala Val Asp Ile Arg Glu Thr Phe Arg Arg Met Ala
                245                 250                 255

Met Asn Asp Val Glu Thr Ala Ala Leu Ile Val Gly Gly His Thr Phe
            260                 265                 270

Gly Lys Thr His Gly Ala Gly Pro Ala Asp Leu Val Gly Pro Glu Pro
        275                 280                 285

Glu Ala Ala Pro Leu Glu Gln Met Gly Leu Gly Trp Lys Ser Ser Tyr
    290                 295                 300

Gly Thr Gly Thr Gly Lys Asp Ala Ile Thr Ser Gly Ile Glu Val Val
305                 310                 315                 320

Trp Thr Asn Thr Pro Thr Lys Trp Asp Asn Ser Phe Leu Glu Ile Leu
                325                 330                 335

Tyr Gly Tyr Glu Trp Glu Leu Thr Lys Ser Pro Ala Gly Ala Trp Gln
            340                 345                 350

Tyr Thr Ala Lys Asp Gly Ala Gly Ala Gly Thr Ile Pro Asp Pro Phe
        355                 360                 365
```

```
Gly Gly Pro Gly Arg Ser Pro Thr Met Leu Ala Thr Asp Leu Ser Leu
    370                 375             380
Arg Val Asp Pro Ile Tyr Glu Arg Ile Thr Arg Arg Trp Leu Glu His
385                 390             395                     400
Pro Glu Glu Leu Ala Asp Glu Phe Ala Lys Ala Trp Tyr Lys Leu Ile
                405             410                 415
His Arg Asp Met Gly Pro Val Ala Arg Tyr Leu Gly Pro Leu Val Pro
            420             425                 430
Lys Gln Thr Leu Leu Trp Gln Asp Pro Val Pro Ala Val Ser His Asp
        435             440             445
Leu Val Gly Glu Ala Glu Ile Ala Ser Leu Lys Ser Gln Ile Arg Ala
    450             455             460
Ser Gly Leu Thr Val Ser Gln Leu Val Ser Thr Ala Trp Ala Ala Ala
465             470             475                     480
Ser Ser Phe Arg Gly Ser Asp Lys Arg Gly Gly Ala Asn Gly Gly Arg
            485             490                 495
Ile Arg Leu Gln Pro Gln Val Gly Trp Glu Val Asn Asp Pro Asp Gly
        500             505             510
Asp Leu Arg Lys Val Ile Arg Thr Leu Glu Glu Ile Gln Glu Ser Phe
        515             520             525
Asn Ser Ala Ala Pro Gly Asn Ile Lys Val Ser Phe Ala Asp Leu Val
    530             535             540
Val Leu Gly Gly Cys Ala Ala Ile Glu Lys Ala Ala Lys Ala Ala Gly
545             550             555                     560
His Asn Ile Thr Val Pro Phe Thr Pro Gly Arg Thr Asp Ala Ser Gln
            565             570             575
Glu Gln Thr Asp Val Glu Ser Phe Ala Val Leu Glu Pro Lys Ala Asp
        580             585             590
Gly Phe Arg Asn Tyr Leu Gly Lys Gly Asn Pro Leu Pro Ala Glu Tyr
        595             600             605
Met Leu Leu Asp Lys Ala Asn Leu Leu Thr Leu Ser Ala Pro Glu Met
    610             615             620
Thr Val Leu Val Gly Gly Leu Arg Val Leu Gly Ala Asn Tyr Lys Arg
625             630             635                     640
Leu Pro Leu Gly Val Phe Thr Glu Ala Ser Glu Ser Leu Thr Asn Asp
            645             650             655
Phe Phe Val Asn Leu Leu Asp Met Gly Ile Thr Trp Glu Pro Ser Pro
            660             665             670
Ala Asp Asp Gly Thr Tyr Gln Gly Lys Asp Gly Ser Gly Lys Val Lys
        675             680             685
Trp Thr Gly Ser Arg Val Asp Leu Val Phe Gly Ser Asn Ser Glu Leu
    690             695             700
Arg Ala Leu Val Glu Val Tyr Gly Ala Asp Asp Ala Gln Pro Lys Phe
705             710             715                     720
Val Gln Asp Phe Val Ala Ala Trp Asp Lys Val Met Asn Leu Asp Arg
            725             730             735
Phe Asp Val Arg
            740
```

( 2 ) INFORMATION FOR SEQ ID NO:22:

( i ) SEQUENCE CHARACTERISTICS:
        ( A ) LENGTH: 15 base pairs
        ( B ) TYPE: nucleic acid
        ( C ) STRANDEDNESS: single ( D ) TOPOLOGY: linear ( i i ) MOLECULE TYPE: DNA ( x i ) SEQUENCE DESCRIPTION: SEQ ID NO:22:

GACGCNNNNN NNNNN   1 5